(12) United States Patent
Dacquay et al.

(10) Patent No.: US 7,887,521 B2
(45) Date of Patent: Feb. 15, 2011

(54) OPHTHALMIC INJECTION SYSTEM

(75) Inventors: Bruno Dacquay, Irvine, CA (US);
Cesario Dos Santos, Aliso Viejo, CA (US); James Foster, Santa Ana, CA (US); Casey Lind, Irvine, CA (US); Raffi Pinedjian, Fountain Valley, CA (US); Robert Sanchez, Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 780 days.

(21) Appl. No.: 11/832,301

(22) Filed: Aug. 1, 2007

(65) Prior Publication Data
US 2009/0036846 A1    Feb. 5, 2009

Related U.S. Application Data

(63) Continuation-in-part of application No. 11/435,906, filed on May 17, 2006, now abandoned.

(60) Provisional application No. 60/921,497, filed on Oct. 16, 2006, provisional application No. 60/921,498, filed on Oct. 16, 2006, provisional application No. 60/921,499, filed on Oct. 16, 2006.

(51) Int. Cl.
*A61M 35/00* (2006.01)
(52) U.S. Cl. .......... 604/294; 604/113; 604/291
(58) Field of Classification Search ........ 604/294, 604/291, 521, 113, 154; 606/28; 128/DIG. 1
See application file for complete search history.

(56) References Cited

U.S. PATENT DOCUMENTS

| | | |
|---|---|---|
| 1,252,614 A | 1/1918 | Pieper |
| 3,089,815 A | 5/1963 | Lieb et al. |
| 3,199,740 A | 8/1965 | Huffa et al. |

(Continued)

FOREIGN PATENT DOCUMENTS

AU    7623298    6/1998

(Continued)

OTHER PUBLICATIONS

"Ultra™ 2800 Positive Displacement Dispenser"; 2004; EFD, Inc. Brochure XP 1104 vol. 11.10; 2 pages.

(Continued)

*Primary Examiner*—Kevin C Sirmons
*Assistant Examiner*—Deanna K Hall
(74) *Attorney, Agent, or Firm*—Kenneth D. Bassinger

(57) ABSTRACT

An ophthalmic injection system has a tip segment attachable to and removable from a limited reuse assembly. The tip segment has a dispensing chamber housing, a plunger, a needle, a temperature control device, a thermal sensor, and a first housing at least partially enclosing the dispensing chamber housing, the temperature control device and the plunger. The limited reuse assembly has an actuator with a shaft, a power source for providing power to the actuator, a controller for controlling the actuator, a mechanical linkage interface, and a second housing at least partially enclosing the power source, the controller, and the actuator. The mechanical linkage interface is coupled to the actuator shaft and has a mating surface on one end. The substance is injected after the temperature of the substance is altered.

31 Claims, 15 Drawing Sheets

U.S. PATENT DOCUMENTS

| | | |
|---|---|---|
| 3,608,549 A | 9/1971 | Merrill |
| 3,858,581 A | 1/1975 | Kamen |
| 3,892,537 A | 7/1975 | Gulati et al. |
| 3,982,537 A | 9/1976 | Bucalo |
| 4,007,742 A | 2/1977 | Banko |
| 4,030,499 A | 6/1977 | Bucalo |
| 4,054,138 A | 10/1977 | Bucalo |
| 4,122,850 A | 10/1978 | Bucalo |
| 4,184,510 A | 1/1980 | Murry et al. |
| 4,246,932 A | 1/1981 | Raines |
| 4,265,618 A | 5/1981 | Herskovitz et al. |
| 4,357,136 A | 11/1982 | Herskovitz et al. |
| 4,392,827 A | 7/1983 | Martin |
| 4,474,752 A | 10/1984 | Haslam et al. |
| 4,484,915 A | 11/1984 | Tartaglia |
| 4,582,488 A | 4/1986 | Newman |
| 4,684,344 A | 8/1987 | Brockway et al. |
| 4,704,088 A | 11/1987 | Newman |
| 4,713,446 A | 12/1987 | DeVore et al. |
| 4,764,165 A | 8/1988 | Reimels et al. |
| 4,795,423 A | 1/1989 | Osterholm |
| 4,830,855 A | 5/1989 | Stewart |
| 4,911,161 A | 3/1990 | Schechter |
| 4,992,045 A | 2/1991 | Beisel |
| 5,066,276 A | 11/1991 | Wang |
| 5,120,307 A | 6/1992 | Wang |
| 5,328,481 A | 7/1994 | Wang |
| 5,336,175 A | 8/1994 | Mames |
| 5,360,413 A | 11/1994 | Leason et al. |
| 5,370,630 A | 12/1994 | Smidebush et al. |
| 5,431,630 A | 7/1995 | Leonard |
| 5,476,511 A | 12/1995 | Gwon et al. |
| 5,487,725 A | 1/1996 | Peyman |
| 5,582,595 A | 12/1996 | Haber et al. |
| 5,602,188 A | 2/1997 | Nakanishi |
| 5,620,700 A | 4/1997 | Berggren et al. |
| 5,662,612 A | 9/1997 | Niehoff |
| 5,743,886 A | 4/1998 | Lynn et al. |
| 5,773,019 A | 6/1998 | Ashton et al. |
| 5,783,205 A | 7/1998 | Berggren et al. |
| 5,824,072 A | 10/1998 | Wong |
| 5,860,949 A | 1/1999 | Chen |
| 5,882,338 A * | 3/1999 | Gray ................... 604/131 |
| 5,928,197 A * | 7/1999 | Niehoff ................ 604/155 |
| 5,928,663 A | 7/1999 | Peyman |
| 5,984,889 A | 11/1999 | Christ et al. |
| 6,051,011 A | 4/2000 | Weidenbenner |
| 6,165,190 A | 12/2000 | Nguyen |
| 6,210,357 B1 | 4/2001 | Morris |
| 6,221,045 B1 | 4/2001 | Duchon et al. |
| 6,270,343 B1 | 8/2001 | Martin |
| 6,290,690 B1 | 9/2001 | Huculak et al. |
| 6,364,865 B1 | 4/2002 | Lavi et al. |
| 6,372,245 B1 | 4/2002 | Bowman et al. |
| 6,372,246 B1 | 4/2002 | Wei et al. |
| 6,413,245 B1 | 7/2002 | Yaacobi et al. |
| 6,419,656 B1 | 7/2002 | Vetter et al. |
| 6,436,143 B1 | 8/2002 | Ross et al. |
| 6,488,659 B1 | 12/2002 | Rosenman |
| 6,520,930 B2 | 2/2003 | Critchlow et al. |
| 6,585,700 B1 | 7/2003 | Trocki et al. |
| 6,595,979 B1 | 7/2003 | Epstein et al. |
| 6,635,267 B1 | 10/2003 | Miyoshi et al. |
| 6,645,179 B1 | 11/2003 | Ishikawa et al. |
| 6,726,654 B2 | 4/2004 | Rosenman |
| 6,940,209 B2 | 9/2005 | Henderson |
| 6,991,457 B2 | 1/2006 | Kazen et al. |
| 7,176,030 B2 | 2/2007 | Faries, Jr. et al. |
| 2002/0055720 A1 | 5/2002 | Hohlfelder et al. |
| 2003/0055380 A1 | 3/2003 | Flaherty |
| 2003/0125665 A1 | 7/2003 | Rosenman |
| 2004/0039253 A1 | 2/2004 | Peyman et al. |
| 2004/0052761 A1 | 3/2004 | Vernon et al. |
| 2004/0054319 A1 | 3/2004 | Langley et al. |
| 2004/0133155 A1 | 7/2004 | Varner et al. |
| 2004/0167466 A1 | 8/2004 | Drasler et al. |
| 2004/0176720 A1 | 9/2004 | Kipfer |
| 2004/0210200 A1 | 10/2004 | Gerondale et al. |
| 2004/0231667 A1 | 11/2004 | Horton et al. |
| 2005/0065477 A1 | 3/2005 | Jost |
| 2005/0177137 A1 * | 8/2005 | Kipfer ................... 604/890.1 |
| 2006/0047250 A1 | 3/2006 | Hickingbotham |
| 2007/0016186 A1 | 1/2007 | LoRusso |
| 2007/0038174 A1 | 2/2007 | Hopkins |
| 2007/0060887 A1 | 3/2007 | Marsh et al. |
| 2007/0142769 A1 | 6/2007 | Griffiths et al. |
| 2007/0270750 A1 | 11/2007 | Dacquay et al. |
| 2009/0069806 A1 | 3/2009 | De La Mora Levy et al. |
| 2009/0254045 A1 | 10/2009 | Jost |

FOREIGN PATENT DOCUMENTS

| | | |
|---|---|---|
| CA | 1313802 | 2/1993 |
| DE | 3434930 A1 | 4/1986 |
| EP | 0348146 A1 | 12/1989 |
| EP | 0356372 A2 | 2/1990 |
| EP | 0398394 | 11/1990 |
| EP | 1704840 A1 | 9/2006 |
| GB | 1551767 | 8/1979 |
| JP | 2002/059055 A | 2/2002 |
| WO | WO 82/03761 A1 | 11/1982 |
| WO | WO 87/00029 A1 | 1/1987 |
| WO | WO 96/03978 A1 | 2/1996 |
| WO | WO 99/33853 A2 | 7/1999 |
| WO | WO 99/65548 | 12/1999 |
| WO | WO 00/74752 A1 | 12/2000 |
| WO | WO 01/10482 A1 | 2/2001 |
| WO | WO 02/07658 A1 | 1/2002 |
| WO | WO 03/006098 | 1/2003 |
| WO | WO 2006/037969 | 4/2006 |
| WO | WO 2006/050008 A1 | 5/2006 |
| WO | WO 2006/067480 | 6/2006 |
| WO | WO 2006/108026 A2 | 10/2006 |

OTHER PUBLICATIONS

"Parker: Your Resource For Motion And Fluid Control Components, Systems and Solutions—System Solutions For Life Sciences"; 2003; Aurora Instruments, LLC Brochure; 8 pages.

U.S. Appl. No. 11/200,452, filed Aug. 9, 2005, Hopkins.

U.S. Appl. No. 11/435,906, filed May 17, 2005, Dacquay, et al.

U.S. Appl. No. 11/486,870, filed Jul. 14, 2006, Marsh, et al.

* cited by examiner

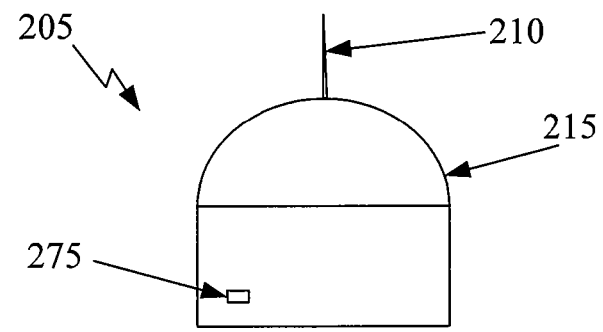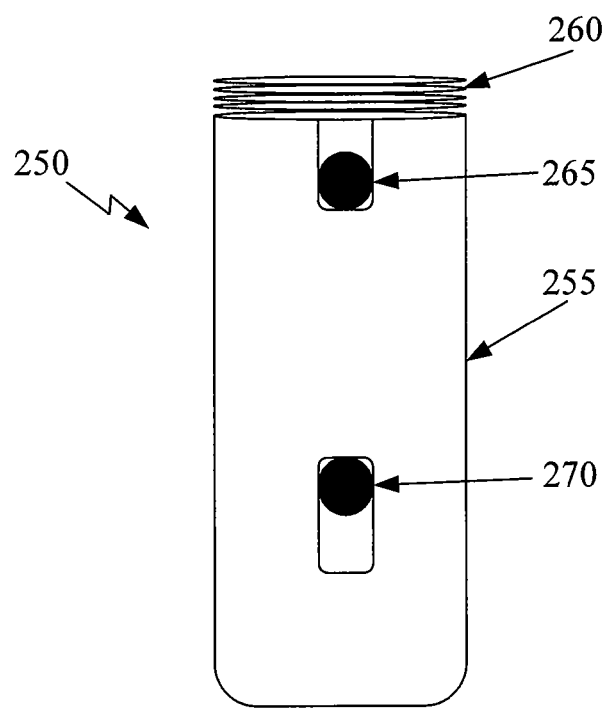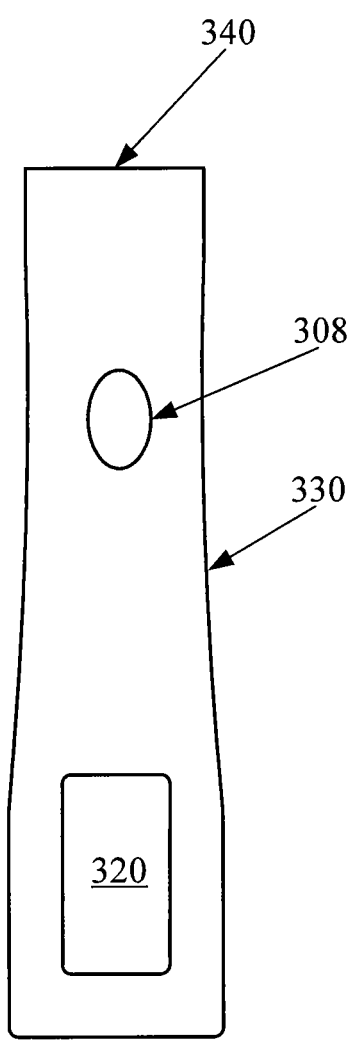
Fig. 2
Fig. 3

US 7,887,521 B2

OPHTHALMIC INJECTION SYSTEM

RELATED APPLICATIONS

This application is a non-provisional of U.S. patent application No. 60/921,497 filed Oct. 16, 2006, U.S. patent application No. 60/921,498 filed Oct. 16, 2006, U.S. patent application No. 60/921,499 filed Oct. 16, 2006, and is a continuation-in-part of U.S. patent application Ser. No. 11/435,906 filed May 17, 2006, now abandoned.

BACKGROUND OF THE INVENTION

The present invention relates to a single-use medical device and more particularly to a two-piece ophthalmic drug delivery device with a disposable tip end containing an improved plunger linkage and seal.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically manually made using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to puncture the eye tissue with the needle, hold the syringe steady, and actuate the syringe plunger (with or without the help of a nurse) to inject the fluid into the eye. The volume injected is typically not controlled in an accurate manner because the vernier on the syringe is not precise relative to the small injection volume. Fluid flow rates are uncontrolled. Reading the vernier is also subject to parallax error. Tissue damage may occur due to an "unsteady" injection. Reflux of the drug may also occur when the needle is removed from the eye.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. Ypsomed, Inc. of Switzerland produces a line of injection pens and automated injectors primarily for the self-injection of insulin or hormones by a patient. This product line includes simple disposable pens and electronically-controlled motorized injectors.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a portable hand piece for injecting a drug into the eye that includes a relatively inexpensive tip segment that can be attached to and removed from a reusable assembly. Placing the more expensive components, including electronics and a drive mechanism, in the reusable assembly, while keeping the sterile components in the tip assembly, improves the efficiency and cost-effectiveness of a drug delivery system. It would be desirable to have a reusable assembly that contains the functionally and components for the injection process. It would also be desirable to have a disposable tip segment that can be easily attached to the reusable assembly for the injection, and then easily removed and discarded after the injection. Such a system provides numerous benefits over prior art injectors.

SUMMARY OF THE INVENTION

In one embodiment consistent with the principles of the present invention, the present invention is an ophthalmic injection system. The ophthalmic injection system has a tip segment attachable to and removable from a limited reuse assembly. The tip segment has a dispensing chamber housing, a plunger, a needle, a temperature control device, a thermal sensor, and a first housing at least partially enclosing the dispensing chamber housing, the temperature control device and the plunger. The dispensing chamber housing has an inner surface and an outer surface. The inner surface partially defines a dispensing chamber for receiving a quantity of a substance. The plunger is engaged with the inner surface of the dispensing chamber housing. is capable of sliding in the dispensing chamber housing, and is fluidly sealed to the inner surface of the dispensing chamber housing. The plunger has a plunger interface. The needle is fluidly coupled to the dispensing chamber. The temperature control device at least partially surrounds the dispensing chamber housing and alters a temperature of the substance in the dispensing chamber. The thermal sensor is located near the dispensing chamber housing and measures a temperature near the dispensing chamber housing. The limited reuse assembly has an actuator with a shaft, a power source for providing power to the actuator, a controller for controlling the actuator, a mechanical linkage interface, and a second housing at least partially enclosing the power source, the controller, and the actuator. The mechanical linkage interface is coupled to the actuator shaft and has a mating surface on one end. The substance is injected after the temperature of the substance is altered.

In another embodiment consistent with the principles of the present invention, the present invention is an ophthalmic injection system. The ophthalmic injection system has a tip segment attachable to and removable from a limited reuse assembly. The tip segment has a dispensing chamber housing, a plunger, a needle, a temperature control device, a thermal sensor, a pair of tip interface connectors, and a first housing at least partially enclosing the dispensing chamber housing, the temperature control device and the plunger. The dispensing chamber housing has an inner surface and an outer surface. The inner surface partially defines a dispensing chamber for holding a quantity of a substance. The plunger is engaged with the inner surface of the dispensing chamber housing, is capable of sliding in the dispensing chamber housing, and is fluidly sealed to the inner surface of the dispensing chamber housing. The plunger has a plunger interface. The needle is fluidly coupled to the dispensing chamber. The temperature control device at least partially surrounds the dispensing chamber housing and alters a temperature of the substance in the dispensing chamber. The thermal sensor is located near the dispensing chamber housing and measures a temperature near the dispensing chamber housing. The pair of tip interface connectors are located on an interfacing surface of the tip segment. The limited reuse assembly has an actuator with a shaft, a power source for providing power to the actuator, a controller for controlling the actuator, a mechanical linkage interface, a pair of limited reuse assembly interface connectors, and a second housing at least partially enclosing the power source, the controller, and the actuator. The mechanical linkage interface is coupled to the actuator shaft and has a mating surface on one end. The pair of limited reuse assembly interface connectors are located on an interfacing surface of the limited reuse assembly. The substance is injected after the temperature of the substance is altered.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 is one view of an ophthalmic medical device including a disposable tip segment and a limited reuse assembly according to an embodiment of the present invention.

FIG. 3 is another embodiment of a limited reuse assembly according to the principles of the present invention.

DETAILED DESCRIPTION OF THE PREFERRED EMBODIMENTS

Figure 1:
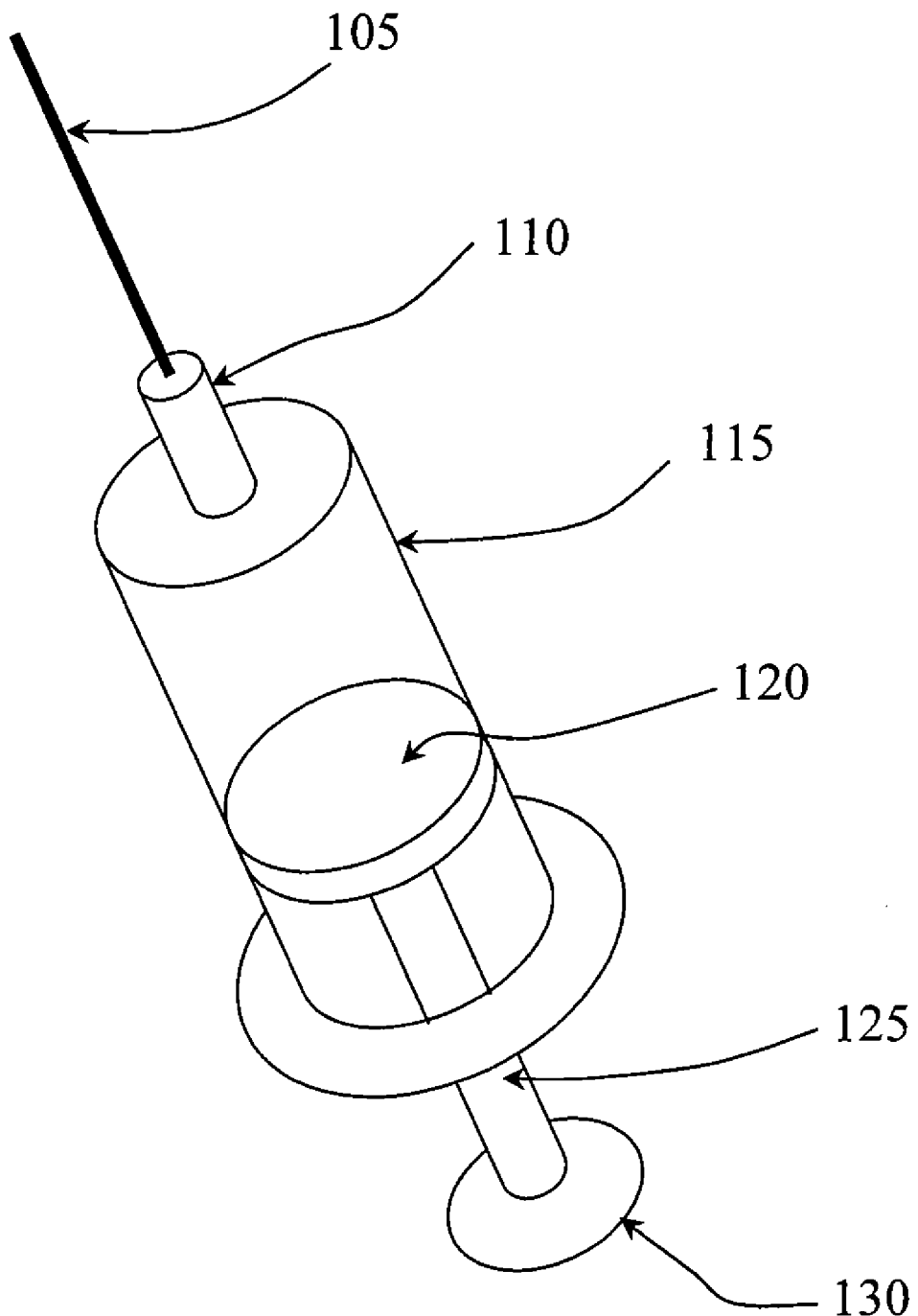
FIG. 1 is a perspective view of a prior art syringe.

Reference is now made in detail to the exemplary embodiments of the invention, examples of which are illustrated in the accompanying drawings. Wherever possible, the same reference numbers are used throughout the drawings to refer to the same or like parts.

FIG. 2 is one view of an ophthalmic medical device including a disposable tip segment and a limited reuse assembly according to an embodiment of the present invention. In FIG. 2, the medical device includes a tip segment 205 and a limited reuse assembly 250. The tip segment 205 includes a needle 210, a housing 215, and an optional light 275. The limited reuse assembly 250 includes a housing 255, a switch 270, a lock mechanism 265, and a threaded portion 260.

Tip segment 205 is capable of being connected to and removed from limited reuse assembly 250. In this embodiment, tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button, a sliding switch, or a cantilevered mechanism. Other mechanisms for connecting tip segment 205 to limited reuse assembly 250, such as those involving structural features that mate with each other, are commonly known in the art and are within the scope of the present invention.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length (for thermal purposes) to facilitate proper delivery of the drug.

Switch 270 is adapted to provide an input to the system. For example, switch 270 may be used to activate the system or to turn on a temperature control device. Other switches, buttons, or user-directed control inputs are commonly known and may be employed with limited reuse assembly 250 and/or tip segment 205.

Optional light 275 is illuminated when tip segment 205 is ready to be used. Optional light 275 may protrude from housing 215, or it may be contained within housing 215, in which case, optional light 275 may be seen through a clear portion of housing 215. In other embodiments, optional light 275 may be replaced by an indicator, such as a liquid crystal display, segmented display, or other device that indicates a status or condition of disposable tip segment 205. For example, optional light 275 may pulse on and off to indicate other states, such as, but not limited to a system error, fully charged battery, insufficiently charged battery or faulty connection between the tip segment 205 and limited use assembly 250. While shown on tip segment 205, optional light 275 or an additional indicator may be located on limited reuse assembly 250.

FIG. 3 is another embodiment of a limited reuse assembly according to the principles of the present invention. Limited reuse assembly 250 includes a button 308, a display 320, and a housing 330. Disposable tip segment 205 attaches to end 340 of limited reuse assembly 250. Button 308 is actuated to provide an input to the system. As with switch 270, button 308 may activate a temperature control device or initiate actuation of a plunger. Display 320 is a liquid crystal display, segmented display, or other device that indicates a status or condition of disposable tip segment 205 or limited reuse assembly 250.

Figure 4:
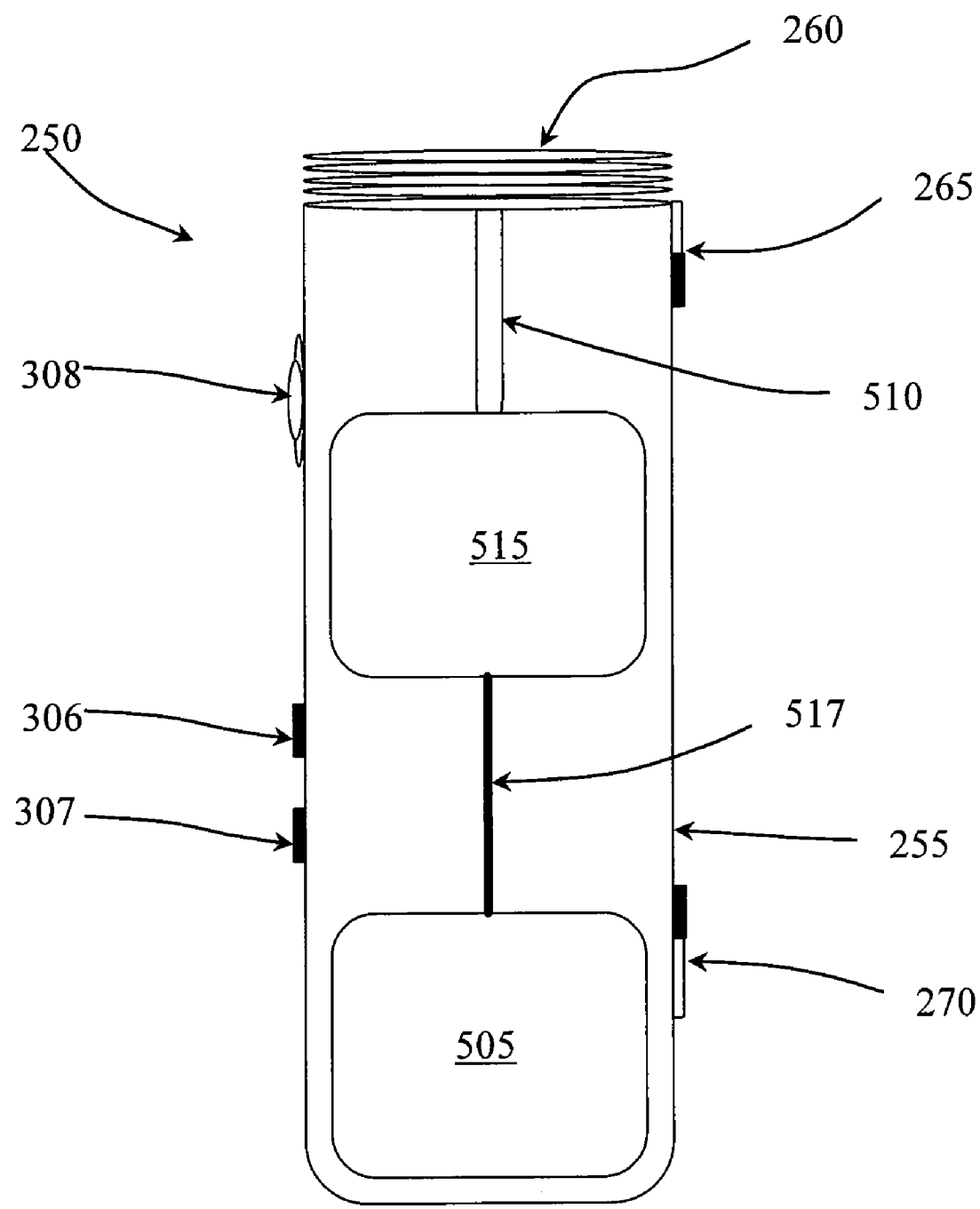
FIG. 4 is a cross section view of another embodiment of a limited reuse assembly according to the principles of the present invention.

FIG. 4 is a cross section view of another embodiment of a limited reuse assembly according to the principles of the present invention. In FIG. 4, power source 505, interface 517, actuator 515, and actuator shaft 510 are located in housing 255. The top part of housing 255 has a threaded portion 260. Lock mechanism 265, switch 270, button 308, and indicators 306, 307 are all located on housing 255.

Power source 505 is typically a rechargeable battery, such as a lithium ion battery, although other types of batteries may be employed. In addition, any other type of power cell is appropriate for power source 505. Power source 505 provides power to the system, and more particularly to actuator 515. Power source 505 also provides power to a tip segment connected to limited reuse assembly 250. In such a case, power source 505 may provide power to a temperature control device (not shown) located in the tip segment. Optionally, power source 505 can be removed from housing 255 through a door or other similar feature (not shown).

Interface 517 is typically an electrical conductor that allows power to flow from power source 505 to actuator 515. Other interfaces, like interface 517, may also be present to provide power to other parts of the system.

Actuator shaft 510 is connected to and driven by actuator 515. Actuator 515 is typically a stepper motor or other type of motor that is capable of moving actuator shaft 510 precise distances. In one embodiment, actuator shaft 510 is connected via a mechanical linkage to a tip segment that delivers a drug into an eye. In such a case, actuator 515 is a stepper motor that can precisely move shaft 510 to deliver a precise quantity of drug into the eye. Actuator 515 is secured to an interior surface of housing 255 by, for example, tabs that engage the outer surface of actuator 515.

In other embodiments, actuator 515 is a linear actuator or linear driver. In such a case, actuator 515 may be a spring or spring driven mechanism, a geared DC motor with a rotary sensor coupled to a linear drive or a dc motor coupled to a linear drive with a linear sensor, or a linear stepper motor. Other types of motors, like a rotational permanent magnet motor, may also be used for actuator 515.

Lock mechanism 265, switch 270, and button 308 are all located on housing 255 so that they can be manipulated by hand. Likewise, indicators 306, 307 are located on housing 255 so that they can be viewed. Lock mechanism 265, switch 270, button 308, and indicators 306, 307 are also connected to a controller (not shown) via interfaces (not shown) located in housing 255.

Figure 5:
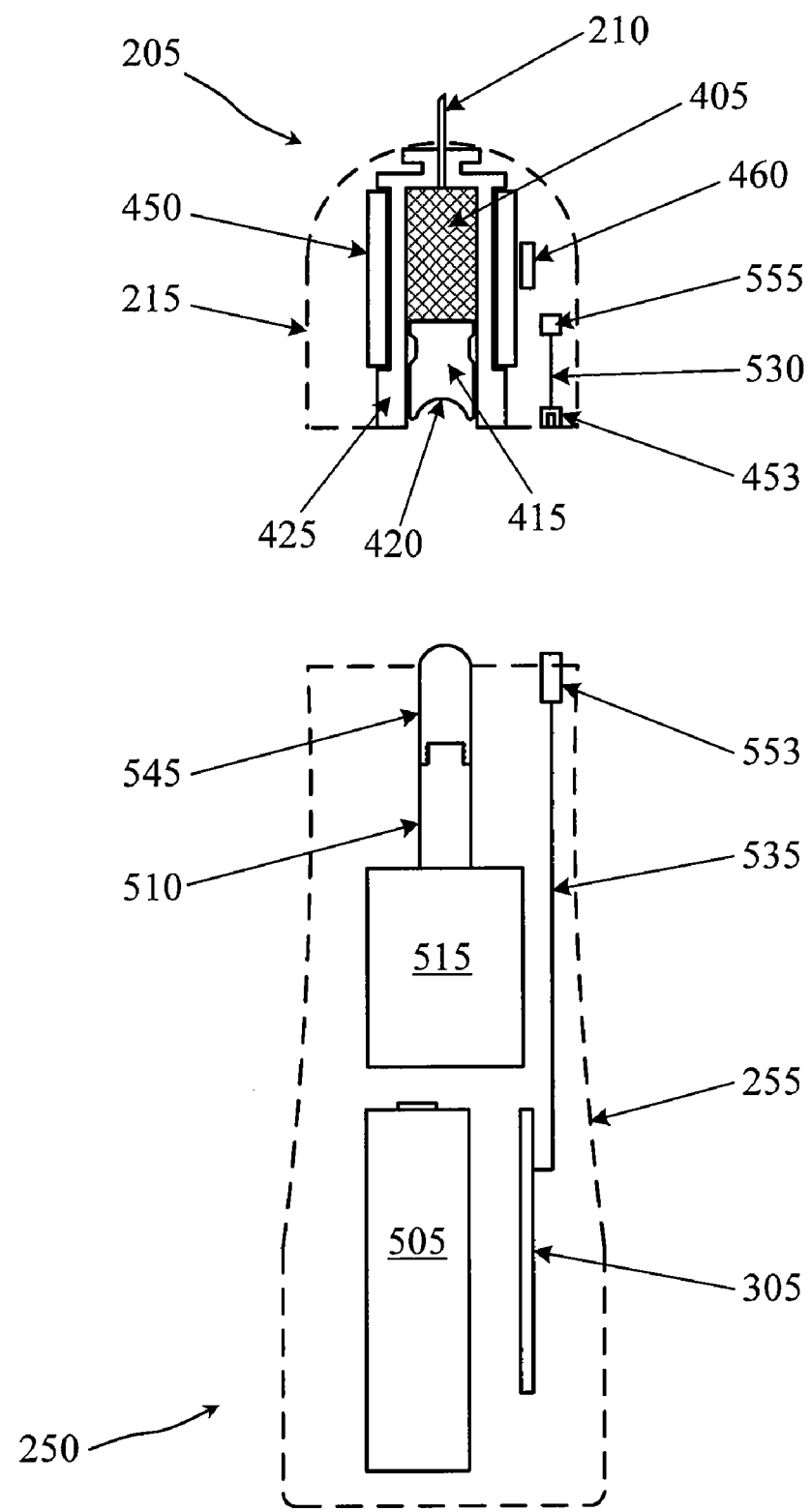
FIG. 5 is a cross section view of a disposable tip segment and a limited reuse assembly according to an embodiment of the present invention.

FIG. 5 is a cross section view of a disposable tip segment and a limited reuse assembly according to an embodiment of the present invention. FIG. 5 shows how tip segment 205 interfaces with limited reuse assembly 250. In the embodiment of FIG. 5, tip segment 205 includes assembly 555, plunger interface 420, plunger 415, dispensing chamber housing 425, tip segment housing 215, temperature control device 450, thermal sensor 460, needle 210, dispensing chamber 405, interface 530, and tip interface connector 453. Limited reuse assembly 250 includes mechanical linkage interface 545, actuator shaft 510, actuator 515, power source 505, controller 305, limited reuse assembly housing 255, interface 535, and limited reuse assembly interface connector 553.

In tip segment 205, plunger interface 420 is located on one end of plunger 415. The other end of plunger 415 forms one end of dispensing chamber 405. Plunger 415 is adapted to slide within dispensing chamber 405. The outer surface of plunger 415 is fluidly sealed to the inner surface of dispensing chamber housing 425. Dispensing chamber housing 425 surrounds the dispensing chamber 405. Typically, dispensing chamber housing 425 has a cylindrical shape. As such, dispensing chamber 405 also has a cylindrical shape. In tip segment 205, assembly 555 includes any number of components as described below.

Needle 210 is fluidly coupled to dispensing chamber 405. In such a case, a substance contained in dispensing chamber 405 can pass through needle 210 and into an eye. Temperature control device 450 at least partially surrounds dispensing chamber housing 425. In this case, temperature control device 450 is adapted to heat and/or cool dispensing chamber housing 425 and any substance contained in dispensing chamber 405. Interface 530 connects temperature control device 450 with tip interface connector 453.

The components of tip segment 205, including dispensing chamber housing 425, temperature control device 450, and plunger 415 are at least partially enclosed by tip segment housing 215. In one embodiment consistent with the principles of the present invention, plunger 415 is sealed to the interior surface of dispensing chamber housing 425. This seal prevents contamination of any substance contained in dispensing chamber 405. For medical purposes, such a seal is desirable. This seal can be located at any point on plunger 415 or dispensing chamber housing 425.

In limited reuse assembly 250, power source 505 provides power to actuator 515. An interface (not shown) between power source 505 and actuator 515 serves as a conduit for providing power to actuator 515. Actuator 515 is connected to actuator shaft 510. When actuator 515 is a stepper motor, actuator shaft 510 is integral with actuator 515. Mechanical linkage interface 545 is connected to actuator shaft 510. In this configuration, as actuator 515 moves actuator shaft 510 upward toward needle 210, mechanical linkage interface 545 also moves upward toward needle 210. In other embodiments of the present invention, mechanical linkage interface 545 and actuator shaft 510 are a single component. In other words, a shaft connected to actuator 515 includes both actuator shaft 510 and mechanical linkage interface 545 as a single assembly.

Controller 305 is connected via interface 535 to limited reuse assembly interface connecter 553. Limited reuse assembly interface connecter 553 is located on a top surface of limited reuse assembly housing 255 adjacent to mechanical linkage interface 545. In this manner, both limited reuse assembly interface connector 553 and mechanical linkage interface 545 are adapted to be connected with tip interface connector 453 and plunger interface 420, respectively.

Controller 305 and actuator 515 are connected by an interface (not shown). This interface (not shown) allows controller 305 to control the operation of actuator 515. In addition, an interface (not shown) between power source 505 and controller 305 allows controller 305 to control operation of power source 505. In such a case, controller 305 may control the charging and the discharging of power source 505 when power source 505 is a rechargeable battery.

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control a temperature control device. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component in FIG. 5, controller 305 may be made of many different components or integrated circuits.

Tip segment 205 is adapted to mate with or attach to limited reuse assembly 250. In the embodiment of FIG. 5, plunger interface 420 located on a bottom surface of plunger 415 is adapted to mate with mechanical linkage interface 545 located near a top surface of limited reuse assembly housing 255. In addition, tip interface connector 453 is adapted to connect with limited reuse assembly interface connector 553. When tip segment 205 is connected to limited reuse assembly 250 in this manner, actuator 515 and actuator shaft 510 are adapted to drive plunger 415 upward toward needle 210. In addition, an interface is formed between controller 305 and temperature control device 450. A signal can pass from controller 305 to temperature control device 450 through interface 535, limited reuse assembly interface connector 553, tip interface connector 453, and interface 530.

In operation, when tip segment 205 is connected to limited reuse assembly 250, controller 305 controls the operation of actuator 515. When actuator 515 is actuated, actuator shaft 510 is moved upward toward needle 210. In turn, mechanical linkage interface 545, which is mated with plunger interface 420, moves plunger 415 upward toward needle 210. A substance located in dispensing chamber 405 is then expelled through needle 210.

In addition, controller 305 controls the operation of temperature control device 450. Temperature control device 450 is adapted to heat and/or cool dispensing chamber housing 425 and its contents. Since dispensing chamber housing 425 is at least partially thermally conductive, heating or cooling dispensing chamber housing 425 heats or cools a substance located in dispensing chamber 405. Temperature information can be transferred from thermal sensor 460 through interface 530, tip interface connector 453, limited reuse assembly interface connector 553, and interface 535 back to controller 305. This temperature information can be used to control the operation of temperature control device 450. When temperature control device 450 is a heater, controller 305 controls the amount of current that is sent to temperature control device 450. The more current sent to temperature control device 450, the hotter it gets. In such a manner, controller 305 can use a feed back loop utilizing information from thermal sensor 460 to control the operation of temperature control device 450. Any suitable type of control algorithm, such as a proportional integral derivative (PID) algorithm, can be used to control the operation of temperature control device 450.

Figure 6:
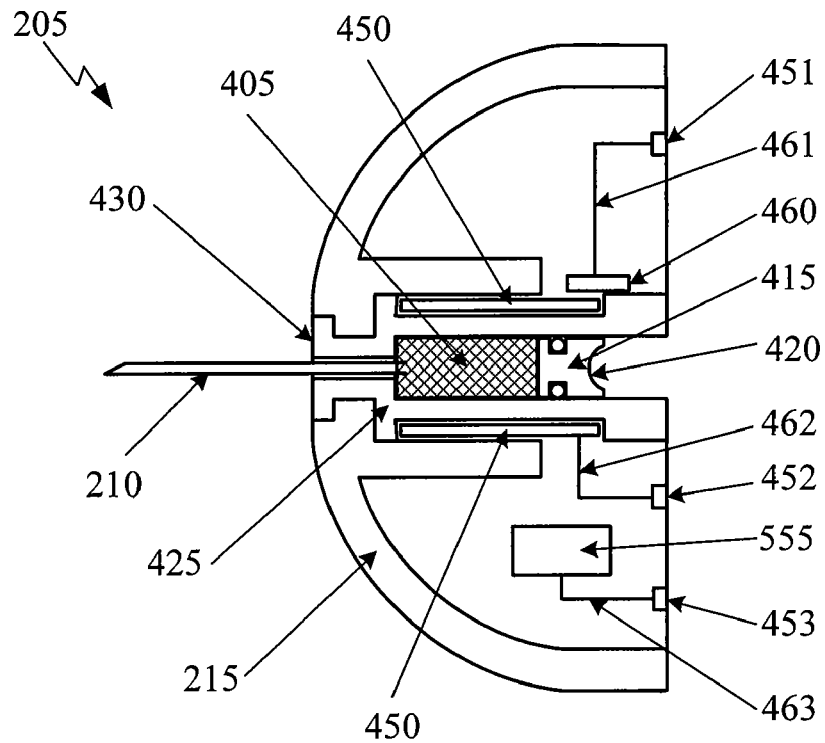
FIG. 6 is a cross section view of a disposable tip segment for an ophthalmic medical device according to an embodiment of the present invention.

FIG. 6 is a cross section view of a disposable tip segment for an ophthalmic medical device according to an embodiment of the present invention. In FIG. 6, disposable tip segment 205 includes housing 215, needle 210, plunger 415, plunger interface 420, dispensing chamber 405, dispensing chamber housing 425, assembly 555, temperature control device 450, thermal sensor 460, optional luer 430, tip interface connectors 451, 452, and 453, and interfaces 461, 462, and 463. Disposable tip segment 205 operates as a disposable injection device.

In the embodiment of FIG. 6, plunger 415 is located in dispensing chamber housing 425. Dispensing chamber 405 is enclosed by dispensing chamber housing 425 and plunger 415. Plunger 415 forms a fluid seal with the interior surface of dispensing chamber housing 425. Needle 210 is fluidly coupled to dispensing chamber 405. In this manner, a substance located in dispensing chamber 405 can be contacted by plunger 415 and pushed out of needle 210. Needle 210 may be secured to disposable tip segment 205 by an optional luer 430 or may be permanently attached. Temperature control device 450 is located on dispensing chamber housing 425 and at least partially surrounds dispensing chamber 405. Housing 215 forms an outer skin on disposable tip segment 205.

In various embodiments of the present invention, temperature control device 450 is a heating and/or a cooling device. Temperature control device 450 is in thermal contact with dispensing chamber housing 425. As such, temperature control device 450 is capable of changing the temperature of the substance in dispensing chamber 405.

In FIG. 6, plunger 415 includes an o-ring. The o-ring seals against an interior surface of dispensing chamber housing 425. In this manner, a sterile seal is maintained thus preventing contamination of the substance in dispensing chamber 405. Plunger 415 may be made of any suitable material, such as, for example, glass, stainless steel, or a polymer. The o-ring is typically made of rubber or a polymer. Other types of seals may also be used. For example, plunger 415 may contain an annular ring that is located around a periphery of plunger 415 so that the annular ring contacts the interior surface of dispensing chamber 425. This annular ring can seal the plunger against the interior surface of dispensing chamber 425. In such a case, the annular ring may be integral with plunger 415, and plunger 415 may be made of rubber or a polymer. Plunger interface 420 may be of any suitable shape. For example, plunger interface may be substantially bowl shaped as shown, or it may be substantially flat, conical, or spherical. It may also include a lip or other similar feature.

Tip interface connectors 451, 452, and 453 serve to provide a connection between tip segment 205 and a limited reuse assembly. Interface 461 connects thermal sensor 460 to tip interface connector 451. Interface 462 connects temperature control device 450 to tip interface connector 452. Interface 463 connects assembly 555 to tip interface connector 453.

Assembly 555 can include any of a number of different components. In one embodiment, assembly 555 contains a fuse that is blown when the heat button is activated or after disposable tip segment 205 is used. In this manner, the fuse prevents reuse of disposable tip segment 205. In another embodiment, assembly 555 includes a memory device that stores information about the type of disposable tip segment 205, dosage information, temperature information, plunger movement information, or any other type of information that identifies a characteristic of disposable tip segment 205 or a manner in which disposable tip segment 205 is operated. In other embodiments, assembly 205 includes a hard-wired memory device, like a NAND flash IC, an RFID tag, a hard-wired wired circuit that can store a representation of data, like a series of fuses and resistors connected in parallel or other type of device.

A substance to be delivered into an eye, typically a drug, is located in dispensing chamber 405. In this manner, the drug is contacted by the inner surface of dispensing chamber housing 425 and one face of plunger 415. Temperature control device 450 is in thermal contact with dispensing chamber housing 425. In this manner, temperature control device 450 is adapted to control the temperature of the contents of dispensing chamber 405.

In various embodiments of the present invention, temperature control device 450 heats a phase transition compound that is located in dispensing chamber 405. This phase transition compound carries a drug that is to be injected into the eye. A phase transition compound is in a solid or semi-solid state at lower temperatures and in a more liquid state at higher temperatures. Such a substance can be heated by temperature control device 450 to a more liquid state and injected into the eye where it forms a bolus that erodes over time. Likewise, a reverse gelation compound may be used. A reverse gelation compound is in a solid or semi-solid state at higher temperatures and in a more liquid state at lower temperatures. Such a compound can be cooled by temperature control device 450 to a more liquid state and injected into the eye where it forms a bolus that erodes over time. As such, temperature control device 450 may be a device that heats a substance in dispensing chamber 405 or a device that cools a substance in dispensing chamber 405 (or a combination of both). After being delivered into the eye, a phase transition compound or reverse gelation compound erodes over time providing a quantity of drug over an extended period of time. Using a phase transition compound or reverse gelation compound provides better drug dosage with fewer injections.

Thermal sensor 460 provides temperature information to assist in controlling the operation of temperature control device 450. Thermal sensor 460 may be located near dispensing chamber housing 425 and measures a temperature near dispensing chamber housing 425. Thermal sensor 460 may also be located in thermal contact with dispensing chamber housing 425, in which case it measures a temperature of dispensing chamber housing 425. In other embodiments, the temperature that thermal sensor 460 measures can be correlated to the temperature of the substance in dispensing chamber 405. In other words, a measurement of the temperature of dispensing chamber housing 425 can be used to calculate the temperature of the substance located in dispensing chamber 405. Since the thermal characteristics of dispensing chamber housing 425 and the substance therein are known, and the temperature of temperature control device 450 is controllable, an application of temperature control device for a specified period of time results in a calculable change in the temperature of the substance in dispensing chamber 405. Thermal sensor 460 may be any of a number of different devices that can provide temperature information. For example, thermal sensor 460 may be a thermocouple or a resistive device whose resistance varies with temperature.

In one embodiment of the present invention, the substance located in dispensing chamber 405 is a drug that is preloaded into the dispensing chamber. In such a case, disposable tip segment 205 is appropriate as a single use consumable product. Such a disposable product can be assembled at a factory with a dosage of a drug installed.

When a drug is preloaded into dispensing chamber 405, a set quantity of the drug can be preloaded. For example, 100 microliters of a drug can be loaded into dispensing chamber 405, and any quantity up to 100 microliters can be dispensed. Information about the amount of drug in dispensing chamber 205 and other dosage information can be stored in assembly 555. In such a case, plunger 415 can be moved a precise distance to deliver a precise dosage of drug from dispensing chamber 405, through needle 210, and into an eye. This provides for flexibility of dosing and for ease of assembly.

Figure 7:
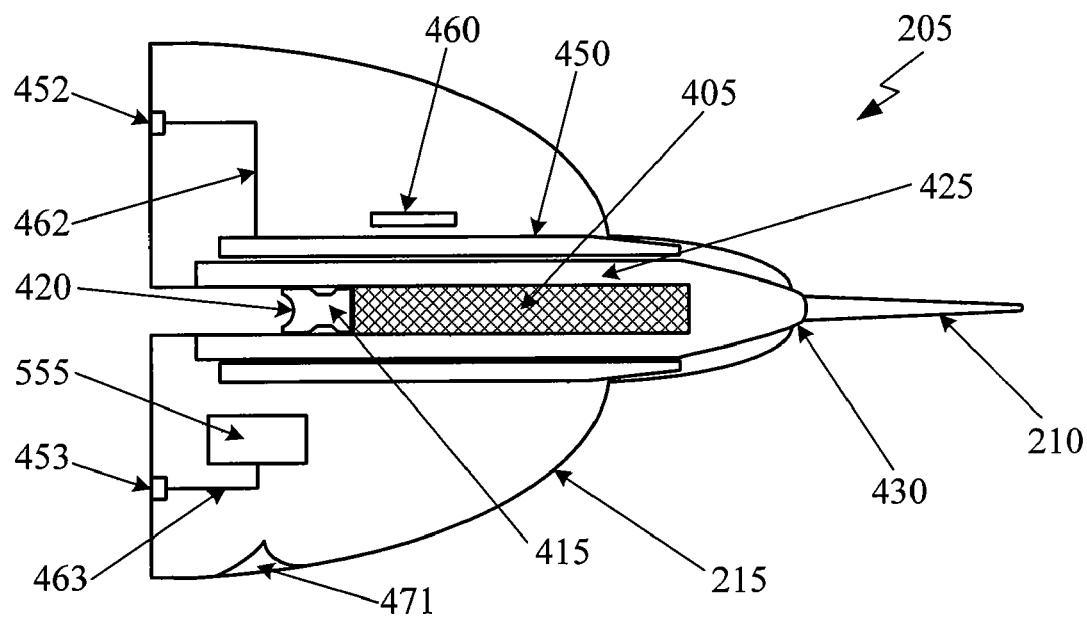
FIG. 7 is a cross section view of a disposable tip segment for an ophthalmic medical device according to an embodiment of the present invention.

FIG. 7 is a cross section view of a disposable tip segment for an ophthalmic medical device according to an embodiment of the present invention. In FIG. 7, disposable tip segment 205 includes housing 215, needle 210, plunger 415, plunger interface 420, dispensing chamber 405, dispensing chamber housing 425, assembly 555, temperature control device 450, thermal sensor 460, optional luer 430, tip interface connectors 452 and 453, interfaces 462 and 463, and lock mechanism 471.

The embodiment of FIG. 7 functions like the embodiment of FIG. 6. The various components of tip segment 205 of FIG. 7 have the same characteristics and operate in substantially the same way as like components of FIG. 6. Lock mechanism 471 serves to attach tip segment 205 to a limited reuse assembly. A mating mechanism, like lock mechanism 265, on a limited reuse assembly, attaches to lock mechanism 471 and secures tip segment 205 to a limited reuse assembly.

Figure 8:
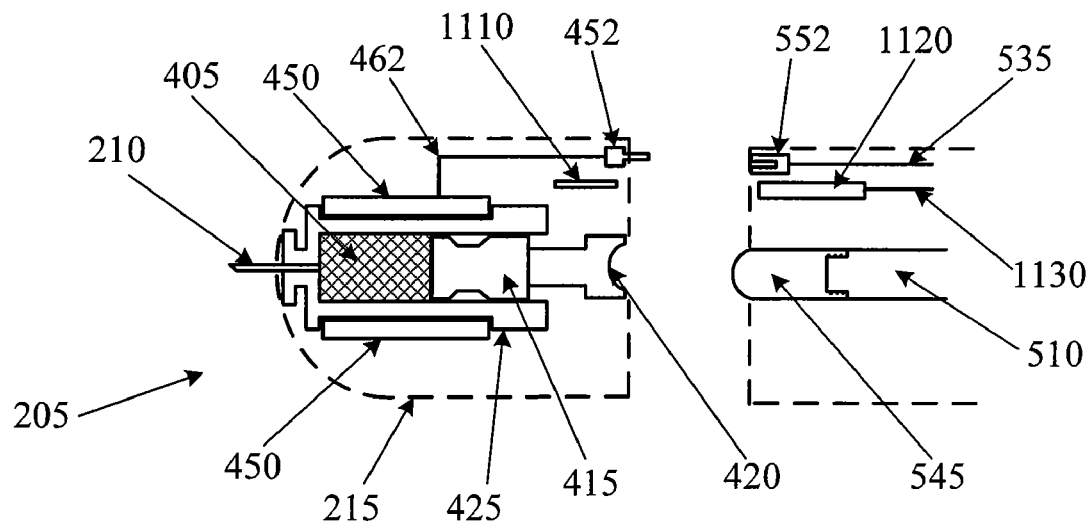
FIG. 8 is a cross section view of a disposable tip segment and a partial view of a limited reuse assembly according to an embodiment of the present invention.

FIG. 8 is a cross section view of a disposable tip segment and a partial view of a limited reuse assembly according to an embodiment of the present invention. In FIG. 7, disposable tip segment 205 includes housing 215, needle 210, plunger 415, plunger interface 420, dispensing chamber 405, dispensing chamber housing 425, RFID tag 1110, temperature control device 450, tip interface connector 452, and interface 462. The partial view of a limited reuse assembly depicts mechanical linkage interface 545, actuator shaft 510, interface 535, limited reuse assembly interface connector 552, RFID reader 1120, and RFID interface 1130.

The embodiment of FIG. 8 functions like the embodiments of FIGS. 6 and 7. The various components of the tip segment 205 of FIG. 8 have the same characteristics and operate in substantially the same way as the like components of FIGS. 6 and 7. However, the embodiment of FIG. 8 uses an RFID system rather than a wired assembly 555 to store and transfer information. RFID reader 1120 is located near the top of a limited reuse assembly adjacent to mechanical linkage interface 545. RFID tag is located at the bottom of tip segment 205. RFID reader 1120 is designed to read information from RFID tag 1110. RFID interface 1130 is connected to controller 305 (not shown).

RFID tag 1110 is configured to hold the same type of information that assembly 555 may hold in the embodiments of FIGS. 5-7. In this manner, RFID tag 1110 is another type of memory. However, as is commonly know, RFID tag 1110 does not require a wired connection to RFID reader 1120. In this manner, a wireless connection between the tip segment 205 (RFID tag 1110) and a limited reuse assembly (RFID reader 1120) can be established.

In one type of RFID system, a passive RFID system, RFID tag 1110 does not have a power supply. Instead, the passive RFID tag relies on the electromagnetic field produced by RFID reader 1120 for its power. The electromagnetic field produced by RFID reader 1120 and emitted from the RFID reader antenna (not shown) induces a small electrical current in RFID tag 1110. This small electrical current allows RFID tag 1110 to operate. In this passive system the RFID tag is designed to collect power from the electromagnetic field emitted by the RFID reader 1120 and to transmit an outbound signal that is received by RFID reader 1120.

In operation the RFID reader antenna (not shown) transmits a signal produced by RFID reader 1120. The RFID tag antenna (not shown) receives this signal and a small current is induced in RFID tag 1110. This small current powers RFID tag 1110. RFID tag 1110 can then transmit a signal through its RFID tag antenna to RFID reader antenna and RFID reader 1120 itself. In this manner, RFID tag 1110 and RFID reader 1120 can communicate with each over a radio frequency link. RFID tag 1110 transmits information, such as dosage information or tip segment information, through RFID tag antenna to RFID reader 1120. This information is received by RFID reader 1120. In this manner, information can be transferred from the tip segment 205 to the limited reuse assembly. RFID reader 1120 can transmit information to RFID tag 1110 in a similar fashion. For example, RFID reader 1120 can transmit information such as dosage information over the radio frequency signal emitted by RFID reader 1120. RFID tag 1120 receives this radio frequency signal with the information. RFID tag 1110 can then store this information.

While the embodiment of FIG. 8 is described as having an RFID system, any other type of wireless system can be used to transfer information between a limited reuse assembly 250 and tip segment 205. For example a Bluetooth protocol maybe used to establish a communications link between a limited reuse assembly 250 and tip segment 205. Information can then be transferred between a limited reuse assembly 250 and a tip segment 205 over this communication link. Other embodiments used to transfer information include an infrared protocol, 802.11, fire wire, or other wireless protocol.

In one embodiment, RFID tag 1110 (or assembly 555) contains dosage information. Information about a proper drug dosage for a drug contained in dispensing chamber 405 may be contained on RFID tag 1110 (or assembly 555). In such a case, controller 305 can read the dosage information from RFID tag 1110 (or assembly 555) and operate actuator 515 in a manner suitable to deliver the proper dosage. For example, 100 microliters may be contained within dispensing chamber 405. Information stating that a dosage of 20 microliters is to be delivered into an eye maybe stored on RFID tag 1110 (or assembly 555). In such a case, controller 305 reads the dosage information (that 20 microliters should be delivered into the eye) from RFID tag 1110 (or assembly 555). Controller 305 can then operate actuator 515 to deliver the 20 microliter dosage. Controller 305 can cause actuator 515 to move actuator shaft 510 and mechanical linkage interface 545 a set distance related to a dosage of 20 microliters. In such a case, plunger 415 is moved this set distance so that only 20 microliters of a drug is expelled from needle 210 and into an eye.

In another embodiment consistent with the principles of the present invention, controller 305 may calculate a distance that plunger 415 must be moved to deliver the desired dosage. For example, if dosage information corresponding to a drug dosage of 20 microliters is read from RFID tag 1110 (or assembly 555) by controller 305, then controller 305 may use this information to calculate a proper distance that plunger 415 must be moved. Since the volume of dispensing chamber 405 as well as the volume of a drug loaded in dispensing chamber 405 is known, a distance that plunger 415 must be moved to deliver that required dosage can be calculated by controller 305. When dispensing chamber 405 has a cylindrical shape, the volume of the dispensing chamber can be calculated by using the cross section area of the cylinder (the area of a circle) times the height of the dispensing chamber. This simple mathematical formula can be used to calculate the total volume of the dispensing chamber 405. Since the cross section area of dispensing chamber 405 is constant for any given application, the height which corresponds to a distance that plunger 415 travels can be calculated for any dosage amount.

For example, assume that 100 microliters of a drug is loaded into dispensing chamber 405 and that the cross sectional area of dispensing chamber 405 is ten. When dispensing chamber 405 is in the shape of a cylinder, the height of that cylinder is also 10. To deliver a dosage of 20 microliters which corresponds to 20% of the total volume of dispensing chamber 405, it is necessary to move plunger 415 upward toward needle 210 a distance of two. In other words, a dosage of 20 microliters corresponds to 20% of the total volume of dispensing chamber 405. In such a case, plunger 415 should be moved upward toward needle 210 a distance equal to 20% of the total height of dispensing chamber 405. Controller 305 can then control actuator 515 such that actuator shaft 510 drives plunger 415 upwards a distance of 20% of the total height of dispensing chamber 405.

In addition, controller 305 may read information about a rate at which plunger 415 should be moved in order to properly deliver a dosage of drug. In such a case, controller 305 reads information about the rate of drug delivery from RFID tag 1110 (or assembly 555) and uses that information to operate actuator 515 to drive plunger 415 at that rate. The rate at which plunger 415 moves may be fixed or variable. In some applications, it may be desirable to move plunger 415 faster than in other applications. For example, when the drug contained in dispensing chamber 405 is a drug that should be heated before being injected into an eye, it maybe desirable to drive plunger 415 at a rate such that the heated drug does not cool and clog needle 210. In other applications, it maybe desirable to move plunger 415 slowly in order to improve the delivery of a drug contained in dispensing chamber 405.

RFID tag 1110 (or assembly 555) may also include any other type of information related to the delivery of a drug. For example, RFID tag 1110 (or assembly 555) may include information about the type of drug contained in dispensing chamber 405, various characteristics of that drug, or other characteristics of a proper dosage or a proper delivery of that drug. In addition, RFID tag 1110 (or assembly 555) may contain safety information, information about the proper operation of tip segment 205, or any other information related to the tip segment or limited reuse assembly.

In another embodiment consistent with the principles of the present invention, a dosage may be selectable by the medical professional who is administering the drug. In such a case, an input device (not shown) located on limited reuse assembly 250 or on tip segment 205 may enable a doctor to select the desired drug dosage. In such a case, controller 305 receives the desired drug dosage and operates actuator 515 to move plunger 415 the required distance to deliver the desired dosage. Such a user selectable dosage scheme may be implemented simply by adding an extra input device.

It may be desirable to include dosage information on RFID tag 1110 (or assembly 555) so that a dosing error is less likely to occur. In such a case, a number of different drug delivery tip segments 205 maybe manufactured and loaded with a drug at the factory. Dosage information can also be loaded onto RFID tag 1110 (or assembly 555) at the factory. In such a case, a number of different tip segments each with the same amount of drug contained in the dispensing chamber 405 but with different dosage information stored on RFID tag 1110 (or assembly 555) can be manufactured and shipped. A doctor can then order the tip segment 205 with the required dosage information on the RFID tag 1110 (or assembly 555). Packaging can be clearly labeled to identify the dosage information so that the proper dosage is administered to a patient.

Figure 9A:
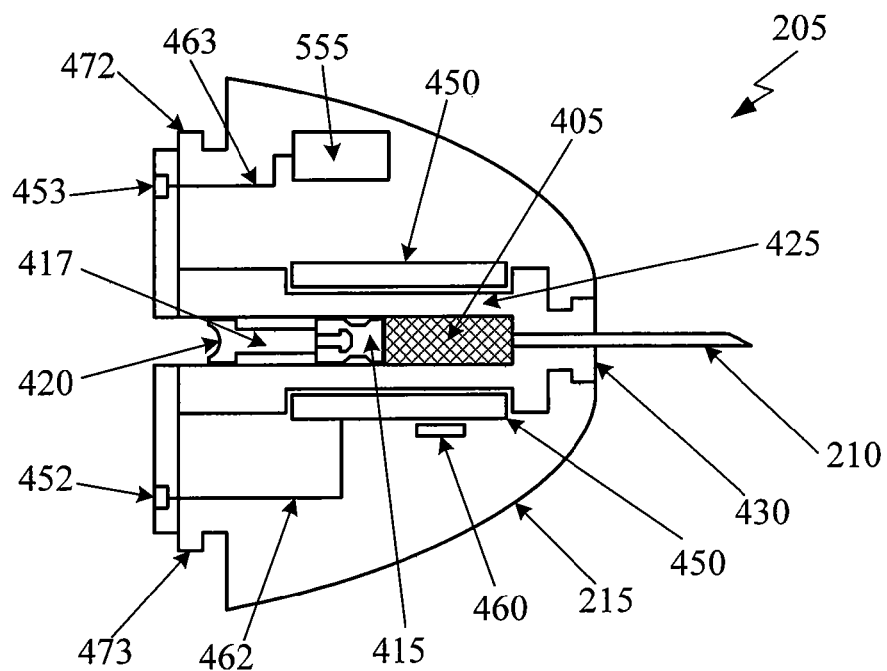
FIG. 9A is a cross section view of a disposable tip segment for an ophthalmic medical device according to an embodiment of the present invention.

FIG. 9A is a cross section view of a disposable tip segment for an ophthalmic medical device according to an embodiment of the present invention. In FIG. 9, disposable tip segment 205 includes housing 215, needle 210, plunger 415, plunger shaft 417, plunger interface 420, dispensing chamber 405, dispensing chamber housing 425, assembly 555, temperature control device 450, thermal sensor 460, optional luer 430, tip interface connectors 452 and 453, interfaces 462 and 463, and tabs 472 and 473.

The various components of tip segment 205 of FIG. 9 have the same characteristics and operate in substantially the same way as like components of FIGS. 5-8. The embodiment of FIG. 9 includes two tabs 472 and 473 that engage slots in a limited reuse assembly. After these two tabs 472 and 473 are inserted into the slots, the tip assembly 205 is rotated to lock it into place on a limited reuse assembly. The two tabs 472 and 473 may be of different shapes or sizes so as to provide a proper interface between tip segment 205 and a limited reuse assembly. When these two tabs 472 and 473 are shaped or sized differently, then tip segment 405 only fits on a limited reuse assembly in one orientation. In other embodiments of the present invention, different shaped or sized tabs can be used with different shaped or sized slots on different limited reuse assemblies. In this manner, a number of different limited reuse assemblies may be manufactured with different shaped or sized slots to accommodate tip segments 205 with complimentary shaped or sized tabs.

In addition, the embodiment of FIG. 9 includes a plunger shaft 417 that is connected to plunger 415. In this embodiment, plunger 415 may be over-molded onto plunger shaft 417. Plunger shaft 417 is generally cylindrical in shape with a middle diameter that is less than a diameter on its distal and proximal ends. Plunger interface 420 is a surface on the proximal end of plunger shaft 417. Plunger shaft 417 is typically made of a rigid material such as stainless steel. Plunger 415 is made of a rubber or polymer material. In another embodiment of the present invention, the distal end of plunger shaft 417 has a lip over which plunger 415 can be applied. Plunger 415 can be press-fitted onto plunger shaft 417 and is retained in place by a lip on the distal end of plunger shaft 417. This allows for easier assembly. Instead of over molding plunger 415 onto a shaft, plunger 415 can be manufactured as a separate part and pushed onto the distal end of plunger shaft 417. Plunger interface 420 can be of any suitable shape.

Figure 9B:
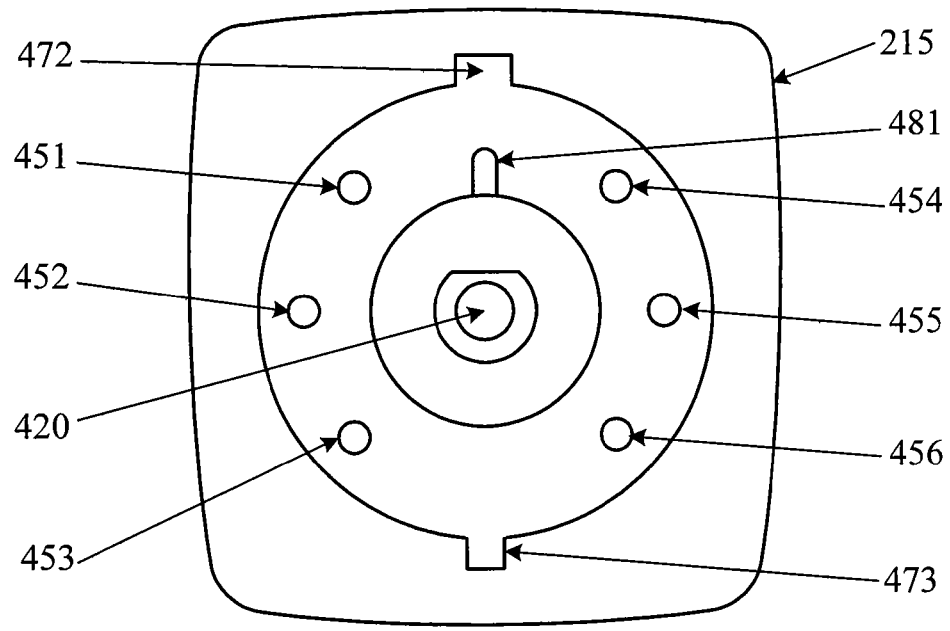
FIG. 9B is an end view of the embodiment of FIG. 9A.

FIG. 9B is an end view of the tip segment of FIG. 9A. FIG. 9B depicts the end of tip segment 205 farthest from needle 210. This end interfaces with a limited reuse assembly. Pictured are housing 215, plunger interface 420, tip interface connectors 451, 452 453, 454, 455, and 456, tabs 472 and 473, and alignment slot 481.

In the embodiment of FIG. 9B, one end of plunger interface 420 is not completely circular. It has a flat portion that is designed to align with a mechanical linkage interface with a similar cross-sectional shape. This optional feature is designed to allow proper alignment of a tip segment and a limited reuse assembly. In other embodiments of the present invention, the cross section view of one end of plunger interface 420 is circular.

Figure 11:
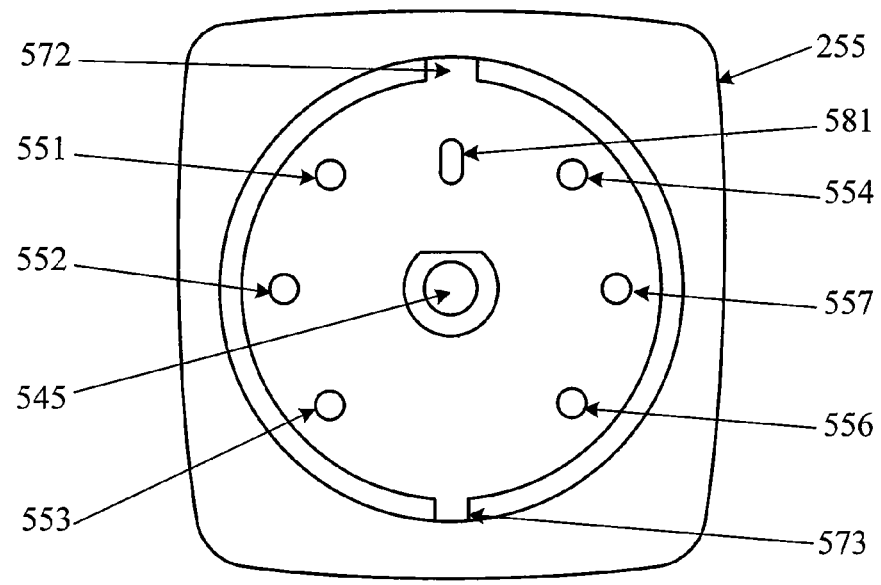
FIG. 11 is end view of a limited reuse assembly according to the principles of the present invention.

The embodiment of FIG. 9B also includes an optional alignment slot 481 to assist in properly aligning a tip segment with a limited reuse assembly. Alignment slot 481 interfaces with an alignment pin on a limited reuse assembly (581 as shown in FIG. 11). In another embodiment of the present invention, tabs 472 and 473 have different sizes. Alternatively, tabs 472 and 473 may have different shapes. The two tabs 472 and 473 also assist in aligning a tip segment with a limited reuse assembly by interfacing with slots 572 and 573 of FIG. 11.

In one embodiment consistent with the principles of the present invention, a tip segment is placed on a limited reuse assembly such that tabs 472 and 473 are inserted into slots 572 and 573. The tip segment is then rotated with respect to the limited reuse assembly so that tabs 472 and 473 are retained in slots 572 and 573. Alignment pin 581 and alignment slot 481 are then properly aligned.

Connectors 451, 452, 453, 454, 455, and 456 electrically link a tip segment to a limited reuse assembly. Connectors 451, 452, 453, 454, 455, and 456 interface with similar connectors 551, 552, 553, 554, 557, and 556, respectively, on a limited reuse assembly (as shown in FIG. 11). These connectors provide a path for signals to pass between a tip segment and a limited reuse assembly.

Figure 10A:
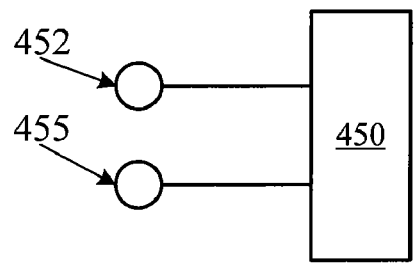
FIGS. 10A-10D are schematic depictions of four different circuits that may be included in embodiments of the present invention.

FIGS. 10A-10D are schematic depictions of four different circuits that may be included in embodiments of the present invention. FIG. 10A shows one of many different configurations for temperature control device 450. In FIG. 10A, temperature control device 450 is connected to connectors 452 and 455. Power and/or control signals are provided to temperature control device 450 through connectors 452 and 455.

Figure 10B:
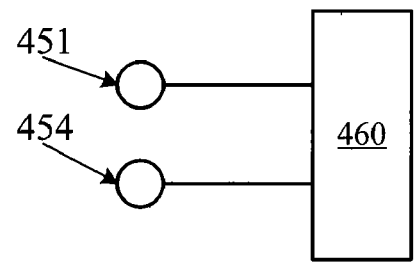

FIG. 10B shows one of many different configurations for thermal sensor 460. In FIG. 10B, thermal sensor 460 is connected to connectors 451 and 454. Signals are received from thermal sensor 460 through connectors 451 and 454.

Figure 10C:
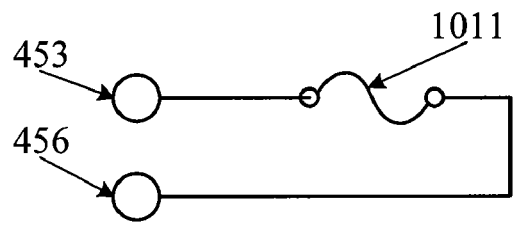

FIG. 10C shows one of many different configurations for a fuse 1011. Fuse 1011 may be contained within assembly 555 or may be implemented as shown in FIG. 10C. In FIG. 10C, fuse 1011 is connected between connectors 453 and 456. In this embodiment, fuse 1011 acts to ensure that the tip assembly is a single-use device. Fuse 1011 is blown when the heat button is activated or after disposable tip segment 205 is used to prevent its reuse. As discussed, a controller in a limited reuse assembly detects when the connected tip segment has been used and directs an increased current to pass through fuse 1011 thus blowing the fuse. When fuse 1011 is blown, the tip segment is no longer operable and must be discarded.

Figure 10D:
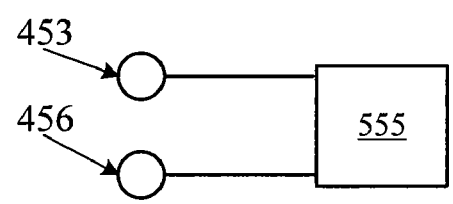

FIG. 10D shows one of many different configurations for assembly 555. In FIG. 10D, assembly 555 is connected to connectors 453 and 456. Power and/or control signals are provided to assembly 555 through connectors 453 and 456.

Many other configurations of connectors 451, 452 453, 454, 455, and 456 may be implemented. For example, while six connectors are shown, any number of connectors may be implemented. Further, any combination of different circuits may be contained in a tip segment.

FIG. 11 is end view of a limited reuse assembly according to the principles of the present invention. The end of the limited reuse assembly shown in FIG. 11 interfaces with the end of the tip assembly shown in FIG. 9B. The end view of limited reuse assembly depicted in FIG. 11 shows housing 255, mechanical linkage interface 545, limited reuse assembly interface connectors 551, 552, 553, 554, 557, and 556, slots 572 and 573, and alignment pin 581.

In the embodiment of FIG. 11, one end of mechanical linkage interface 545 is not completely circular. It has a flat portion that is designed to align with a plunger interface with a similar cross-sectional shape. This optional feature is designed to allow proper alignment of a tip segment and a limited reuse assembly. In other embodiments of the present invention, the cross section view of one end of mechanical linkage interface 545 is circular.

The embodiment of FIG. 11 also includes an optional alignment slot 581 to assist in properly aligning a tip segment with a limited reuse assembly. Alignment pin 581 interfaces with an alignment slot on a tip segment (481 as shown in FIG. 9B). In another embodiment of the present invention, slots 572 and 573 have different sizes. Alternatively, slots 572 and 573 may have different shapes. The two slots 572 and 573 also assist in aligning a tip segment with a limited reuse assembly by interfacing with tabs 472 and 473 of the tip segment shown in FIG. 9B.

Connectors 551, 552, 553, 554, 557, and 556 electrically link a tip segment to a limited reuse assembly. Connectors 551, 552, 553, 554, 557, and 556 interface with connectors 451, 452 453, 454, 455, and 456 on a tip segment (as shown in FIG. 9B). These connectors provide a path for signals to pass between a tip segment and a limited reuse assembly.

Figures 12, 13:
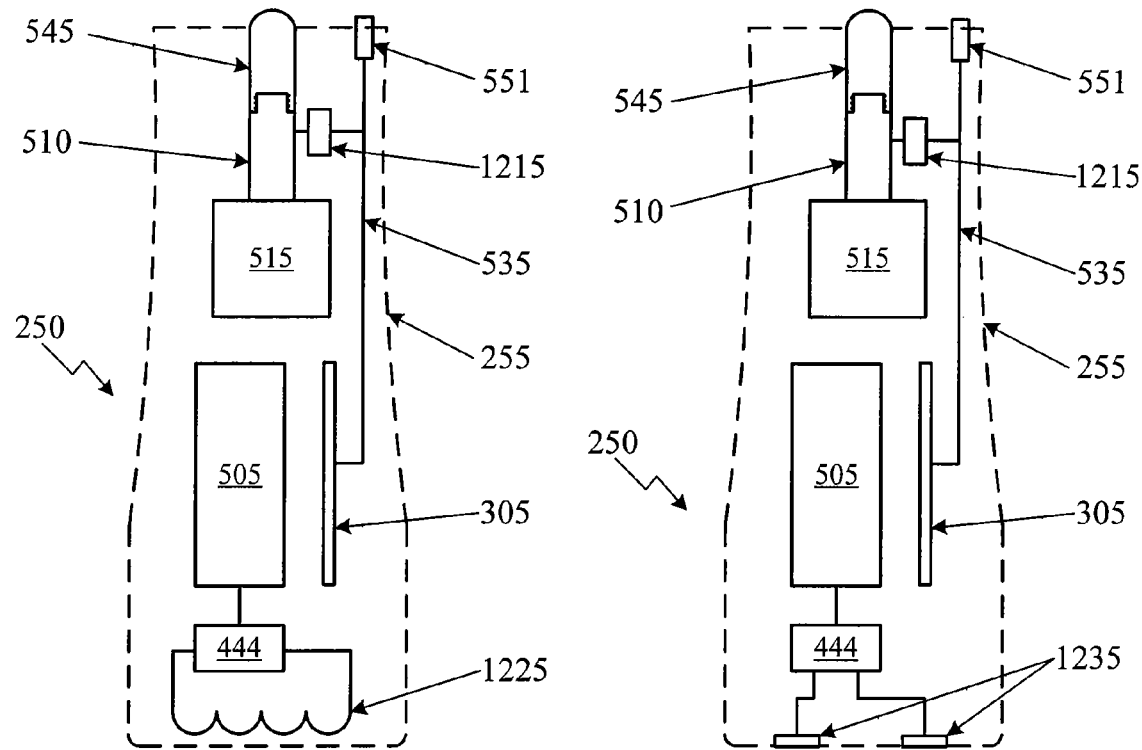
FIG. 12 is a cross section view of a limited reuse assembly according to an embodiment of the present invention.
FIG. 13 is a cross section view of a limited reuse assembly according to an embodiment of the present invention.

FIG. 12 is a cross section view of a limited reuse assembly according to an embodiment of the present invention. In FIG. 12, limited reuse assembly 250 includes mechanical linkage interface 545, actuator shaft 510, actuator 515, power source 505, controller 305, limited reuse assembly housing 255, interface 535, limited reuse assembly interface connector 551, displacement sensor 1215, power source controller 444, and inductive element 1225.

Displacement sensor 1215 measures the movement of actuator shaft 510. Displacement sensor may be, among other things, an optical rotary encoder, a linear encoder, a current sensing circuit (Hall sensor), a rotary potentiometer, or a linear potentiometer. In other embodiments, displacement sensor is capable of detecting if actuator 515 stalls. For example, a Hall sensor can detect an increased current draw by actuator 515 that indicates a stall condition. Displacement sensor 1215 may also measure back EMF from actuator 515. Displacement sensor 1215 may be comprised of a single component or multiple components. In one embodiment consistent with the principles of the present invention, displacement sensor 1215 includes a device to measure the distance that actuator shaft 510 travels and a device to detect if actuator 515 stalls.

Displacement sensor 1215 measures the position of actuator shaft 510. Since mechanical linkage interface 545 is connected to actuator shaft 510, displacement sensor 1215 also measures its position. Such a displacement sensor 1215 can be used to determine if a full dosage is delivered. If displacement sensor 1215 detects that actuator shaft 510 has traveled a certain distance corresponding to a movement of mechanical linkage interface 545 and plunger 415, then it is known that a certain dosage has been expelled from needle 210. In the case where a drug is to be delivered into an eye, displacement sensor 1215 provides information about the movement of actuator shaft 510 that can be used to determine if the full dosage has been delivered.

In some cases, actuator 515 may stall, thus failing to drive actuator shaft 510, mechanical linkage interface 545, and plunger 415 the proper distance to deliver a full dosage of a drug into an eye. In such a case, displacement sensor 1215 measures the distance that actuator shaft 510, mechanical linkage interface 545, and plunger 415 have traveled. From this distance information, a delivered amount of drug can be calculated. For example, when the dispensing chamber 405 is cylindrical in shape, its circular cross-sectional area is known. The distance measured by displacement sensor 1215 then becomes the height of the cylinder, and the volume of displacement can be easily calculated (by controller 305, for example). This delivered amount can be communicated, along with a stall indication, via a display, such as display 320 (FIG. 3).

Displacement sensor 1215 may also provide other information useful in the drug delivery process. For example, when a tip segment is connected to a limited reuse assembly, actuator shaft 510 may be withdrawn or brought to a homed position for connection of a tip segment. Displacement sensor 1215 can measure the movement of actuator shaft 510 to this homed position. Actuator shaft 510 may be placed in a homed position to allow a tip segment to be attached to a limited reuse assembly or prior to delivery of a drug. In one embodiment, information read from displacement sensor 1215 is used to confirm that actuator shaft 510 is in a homed position before actuator 515 is activated to deliver a drug into the eye.

The embodiment of FIG. 12 also includes power source controller 444 and inductive element 1225. These two components control the charging of power source 505 when power source 505 is, for example, a rechargeable battery. Power source controller 444 includes circuitry that may perform any of a number of different functions related to the charging, monitoring, and maintenance of power source 505. In other embodiments, power source controller 444 may be implemented in or integrated into controller 305.

In one embodiment of the present invention, power source controller 444 (or controller 305, as the case may be) counts the number of times that limited reuse assembly 250 has been used. After the count has reached a predetermined safe number of uses, limited reuse assembly 250 is disabled. Alternatively, power source controller 444 (or controller 305, as the case may be) counts the number of times power source 505 has been charged (the number of charge cycles to which power source 505 has been subjected). When the count reaches a predetermined threshold, limited reuse assembly 250 is disabled. In other embodiments of the present invention power source controller 444 (or controller 305, as the case may be) detects fault conditions or other unsafe conditions of power source 505 and prevents further use of limited reuse assembly 250.

To charge power source 505, a current is induced in inductive element 1225 when it is placed near another inductive element in a charging base (not shown). This induced current charges power source 505.

FIG. 13 is a cross section view of a limited reuse assembly according to an embodiment of the present invention. In FIG. 12, limited reuse assembly 250 includes mechanical linkage interface 545, actuator shaft 510, actuator 515, power source 505, controller 305, limited reuse assembly housing 255, interface 535, limited reuse assembly interface connector 551, displacement sensor 1215, power source controller 444, and charging contacts 1235.

In the embodiment of FIG. 13, contacts 1235 interface with contacts on a charging base (not shown) to provide power to power source 505. In one embodiment, contacts 1235 are a USB-type connection such as those used by portable electronic devices with docking stations. In one embodiment, a Molex™ CradleCon™ connector is employed. Other types of connectors may also be used.

Figure 14:
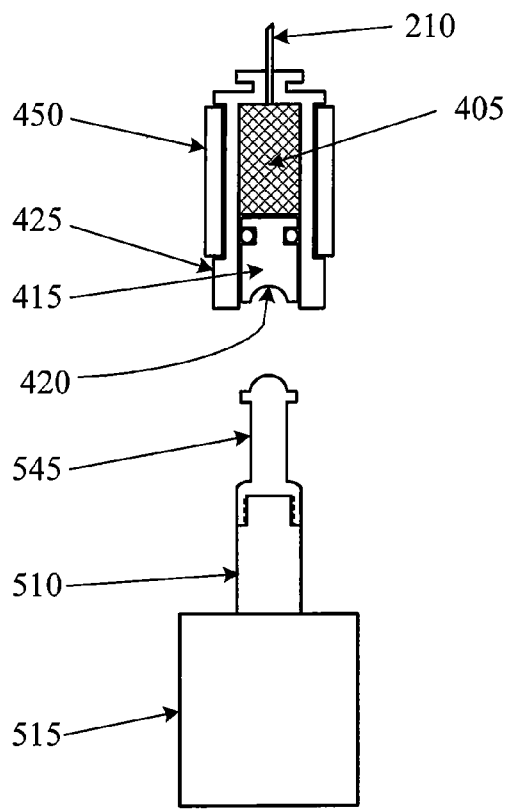
FIGS. 14 and 15 are cross section views of two subassemblies according to the principles of the present invention.
Figure 15:
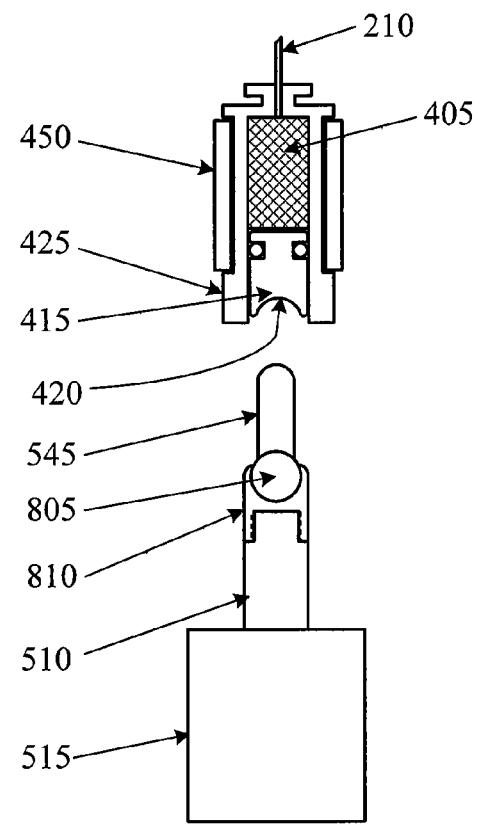

FIGS. 14 and 15 are cross section views of two subassemblies according to the principles of the present invention. Each of these subassemblies depicts the path from the actuator 515 to the needle 210. FIG. 14 depicts a mechanical linkage interface 545 that is rigidly connected to actuator shaft 510, while FIG. 15 depicts a mechanical linkage assembly 545 with a ball joint 805. The use of ball joint 805 assists in aligning mechanical linkage interface 545 with plunger interface 420.

In FIG. 14, actuator 515 has an actuator shaft 510 that is rigidly connected to mechanical linkage interface 545. Mechanical linkage interface mates with plunger interface 420. Plunger 415 is disposed within dispensing chamber housing 425 and is sealed against an inside surface of dispensing chamber housing 425. Dispensing chamber 405 is bounded by an interior surface of dispensing chamber housing 425 and the distal face of plunger 415. Temperature control device 450 at least partially surrounds dispensing chamber housing 425. Needle 210 is fluidly coupled to dispensing chamber 405.

In FIG. 15, actuator 515 has an actuator shaft 510 that is connected to shaft 810 via a ball joint. Mechanical linkage interface 545 is rotatably connected to shaft 810 via ball joint 805. Mechanical linkage interface mates with plunger interface 420. Plunger 415 is disposed within dispensing chamber housing 425 and is sealed against an inside surface of dispensing chamber housing 425. Dispensing chamber 405 is bounded by an interior surface of dispensing chamber housing 425 and the distal face of plunger 415. Temperature control device 450 at least partially surrounds dispensing chamber housing 425. Needle 210 is fluidly coupled to dispensing chamber 405.

In FIGS. 14 and 15, actuator 515 drives actuator shaft 510 upward (in a direction towards needle 210). In turn, mechanical linkage interface 545 is also driven upward. When mechanical linkage interface 545 is mated with plunger interface 420, plunger 420 is also moved upward. A substance contained in dispensing chamber 405 is expelled through needle 210. In this manner, motion and force is transferred from actuator shaft 510 to mechanical linkage interface 545 to plunger 415.

When dispensing chamber 405 contains a drug that is to be delivered into an eye, the configurations of FIGS. 14-15 eliminate reflux when the needle is removed from the eye. Motion of the plunger 415 is in a single direction (a direction that expels the drug in dispensing chamber 405). When mechanical linkage interface 545 is moved in a direction away from needle 210, for example, after the drug has been injected into the eye, the plunger 415 remains in place. Since plunger 415 is not rigidly connected to mechanical linkage interface 545, plunger 415 is not retracted as mechanical linkage interface 545 is retracted.

Figure 16:
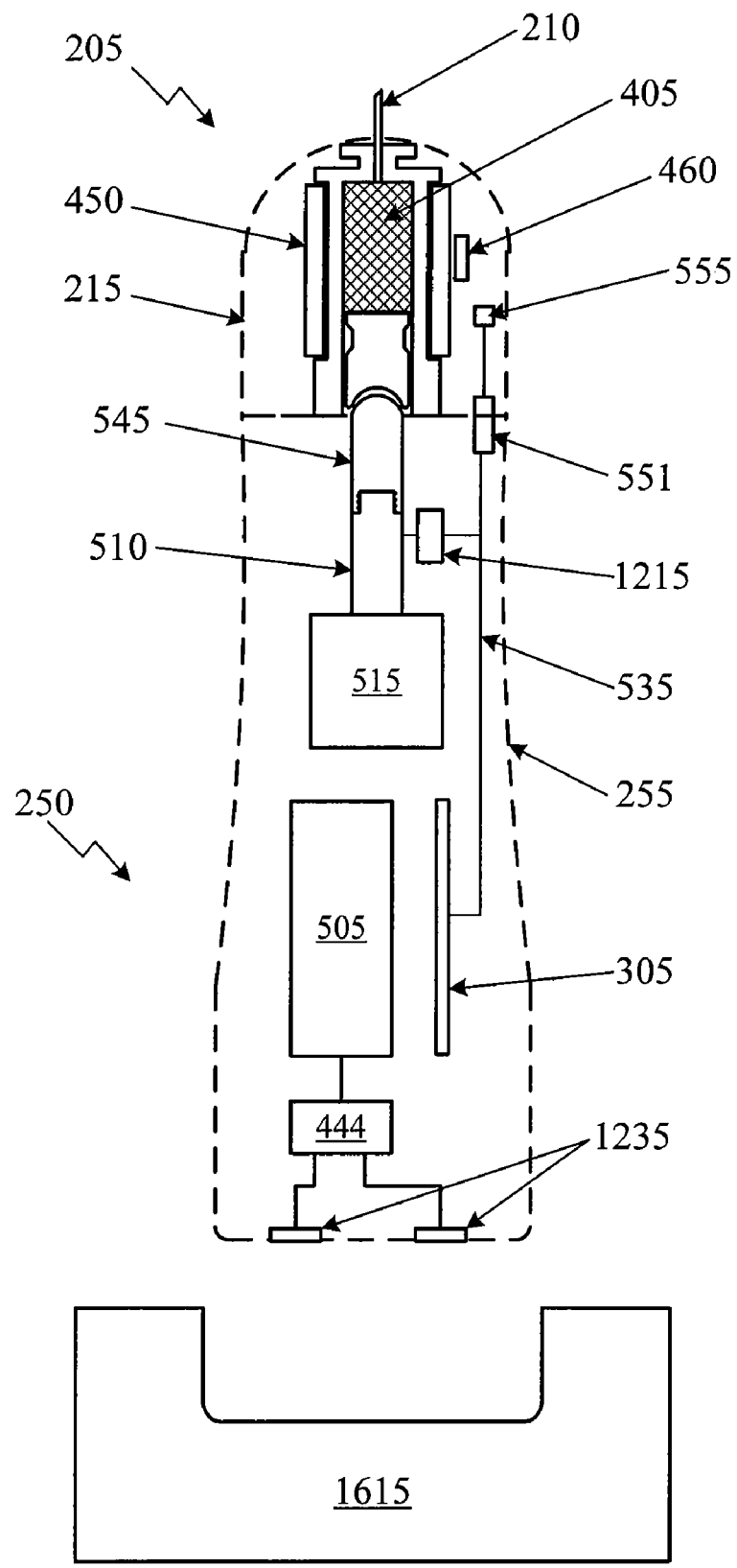
FIG. 16 is a cross section view of a limited reuse assembly, tip segment, and a charging base according to the principles of the present invention.

FIG. 16 is a cross section diagram of the limited reuse assembly of FIG. 13 and a charging base. In FIG. 16, a bottom surface of limited reuse assembly 250 interfaces with charging base 1615. When limited reuse assembly 250 is resting in charging base 1615, power source 505 can be charged. After being charged, limited reuse assembly 250 can be removed from charging base 1615. In one embodiment of the present invention, limited reuse assembly 250 with an attached tip segment 205 is placed in charging base 1615 and a substance located in dispensing chamber 405 is heated or cooled by temperature control device 450. In this manner, charging base 1615 provides the power for temperature control device 450. When the substance located in dispensing chamber 405 has reached the proper temperature (as determined from information from thermal sensor 460), limited reuse assembly 250 with attached tip segment 205 can be removed from the charging base. This saves power source 505 for the injection process when limited reuse assembly 250 and attached tip segment 205 are removed from charging base 1615.

Figure 17A:
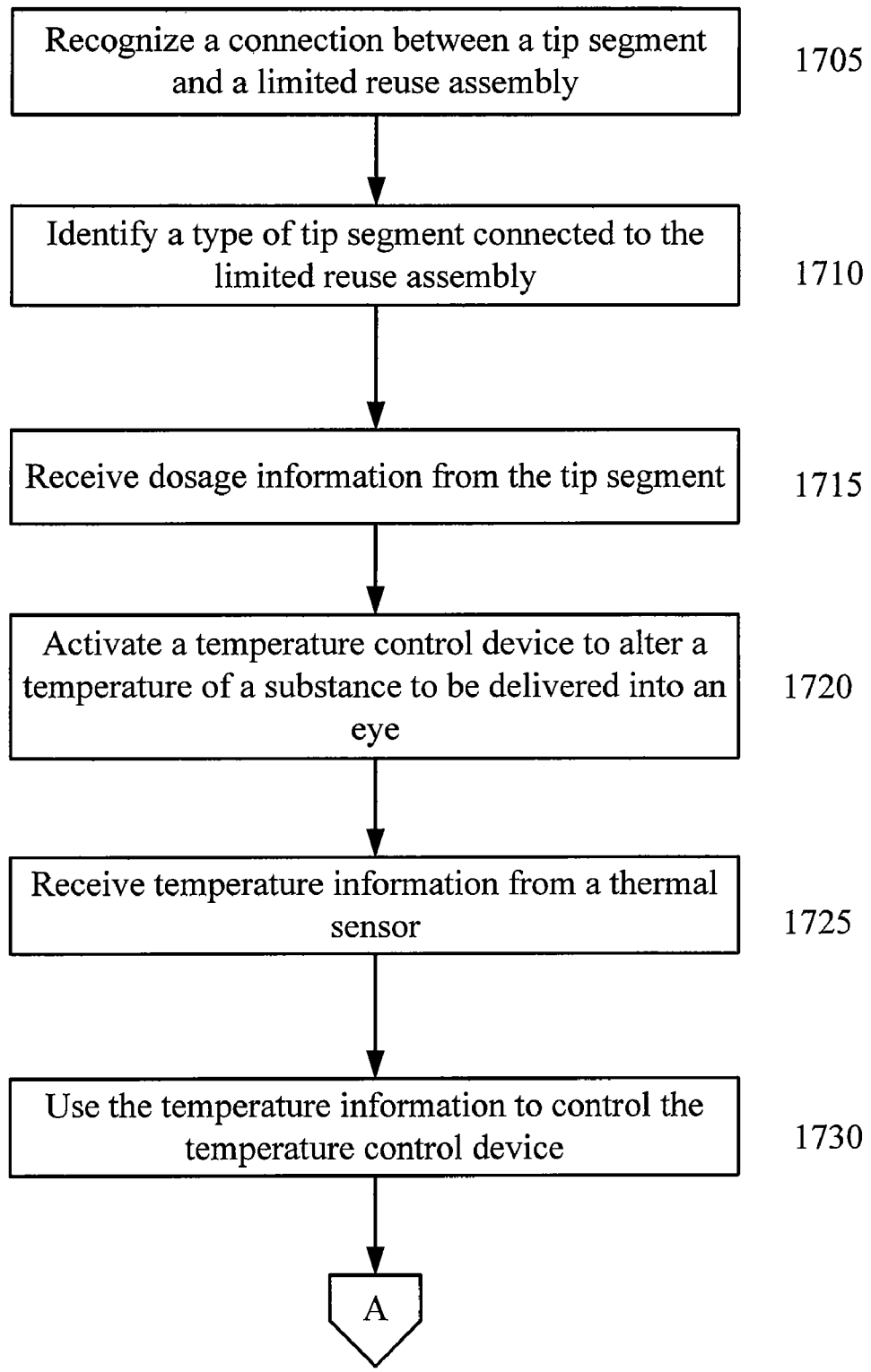
FIGS. 17A and 17B are flow charts of one method of injecting a substance into an eye according to the principles of the present invention.
Figure 17B:
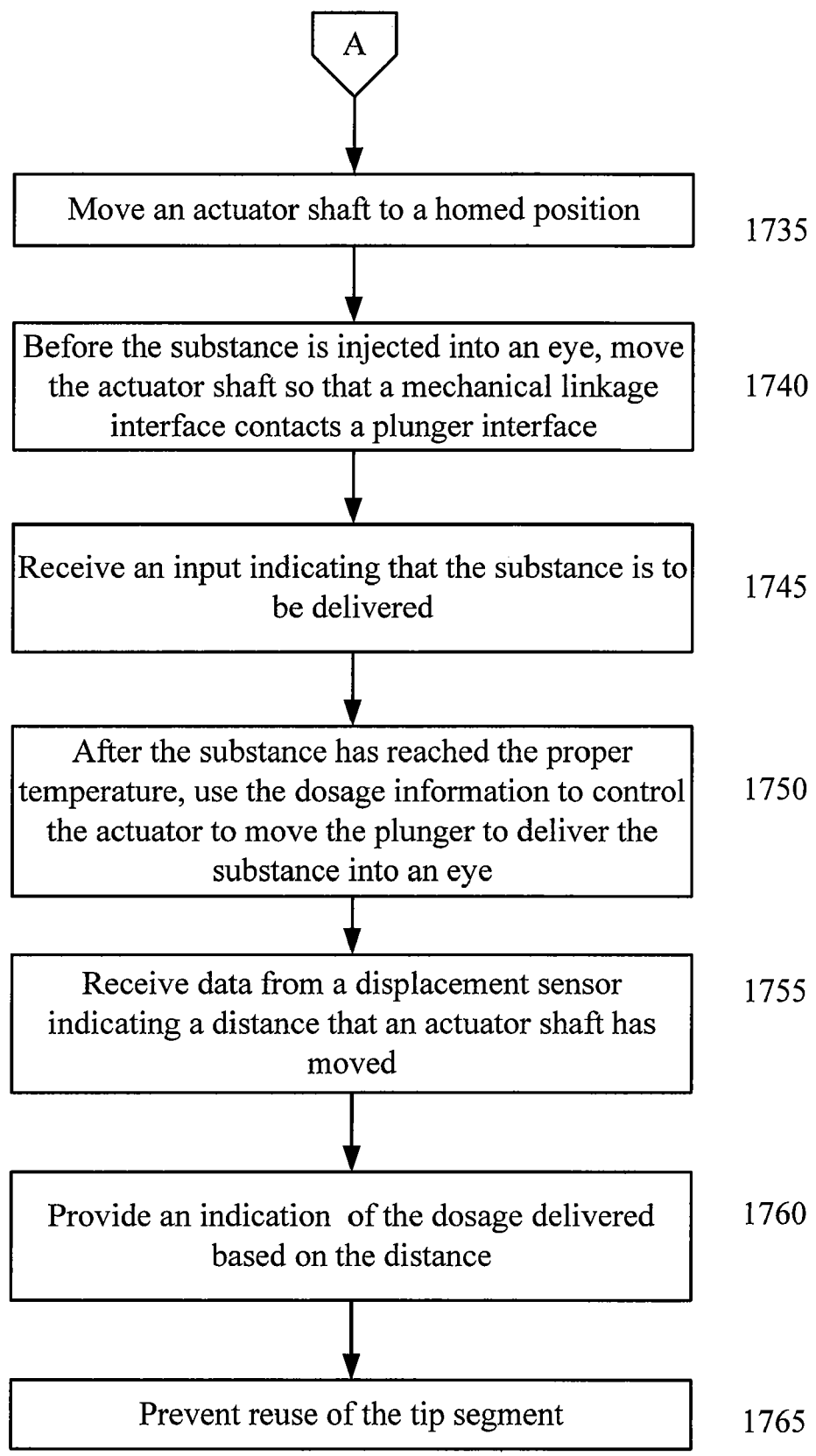

FIGS. 17A and 17B are flow charts of one method of injecting a substance into an eye according to the principles of the present invention. In 1705, a connection between a tip segment and a limited reuse assembly is recognized. In 1710, the type of tip segment that was connected to the limited reuse assembly is identified. For example, a drug delivery tip segment or type of drug delivery tip segment may be identified. Such identification may occur by reading information from the tip segment, for example, by reading information from memory or RFID tag. In 1715, dosage information is received from the tip segment. Like the information relating to the type of tip segment, dosage information may be read from a memory device in the tip segment by a controller, RFID reader, or similar device in the limited reuse assembly.

In 1720, a temperature control device is activated to alter the temperature of the substance that is located in the dispensing chamber. The substance may be heated or cooled as previously described. In addition, the heating or cooling may only take place when the tip segment and limited reuse assembly are located on a charging base. In 1725, temperature information is received from a thermal sensor that is located near the dispensing chamber in which the substance is located. In 1730, this temperature information is used to control the temperature control device to regulate the temperature of the substance.

In 1735, the actuator shaft is moved to a homed position. For example, the actuator shaft may be completely retracted to establish a homed position. The homed position can establish a reference point for a displacement sensor. In other words, the displacement sensor can begin measuring movement of the actuator shaft from the homed position. In 1740, the actuator shaft is moved until the mechanical linkage interface (which is integral with or connected to the actuator shaft) contacts the plunger interface. In this position, any further movement of the actuator shaft results in an expulsion of the substance from the dispensing chamber. When the mechanical linkage interface is in contact with the plunger interface, the device is ready to be used to inject the substance into the eye. This step is taken before injecting the substance into the eye so that the substance can be maintained at a proper temperature for the injection. For example, the substance may be heated or cooled while the tip segment and limited reuse assembly are located on a charging base. When the tip segment and limited reuse assembly are removed from the charging base, the doctor may have a limited period of time to perform the injection before the temperature of the substance falls outside of the proper temperature range. Having the mechanical linkage interface in contact with the plunger interface allows for an injection to be performed in a short amount of time.

In 1745, an input is received indicating that the substance is to be delivered into the eye. For example the doctor may press a button that sends a signal to the controller indicating that the actuator is to be activated to deliver the substance. In 1750, the dosage information is used to control the operation of the actuator to deliver the proper dosage at the proper rate. The substance is delivered into they eye only after it is in the proper temperature range. In 1755, information is received from the displacement sensor. This information indicates how far the actuator shaft has traveled. The distance the actuator shaft has traveled correlates to a dosage. The further the shaft has traveled, the more the plunger has been displaced, and the greater the dosage delivered. In 1760, an indication of the dosage delivered is provided. For example, a successful injection, in which the complete dosage has been successfully delivered, may be indicated by a green light or by a number (representing the amount of substance delivered in microliters). In an unsuccessful injection, the amount of substance actually delivered is displayed. In 1765, reuse of the tip segment is prevented, for example, by blowing a fuse in the tip segment.

Figure 18:
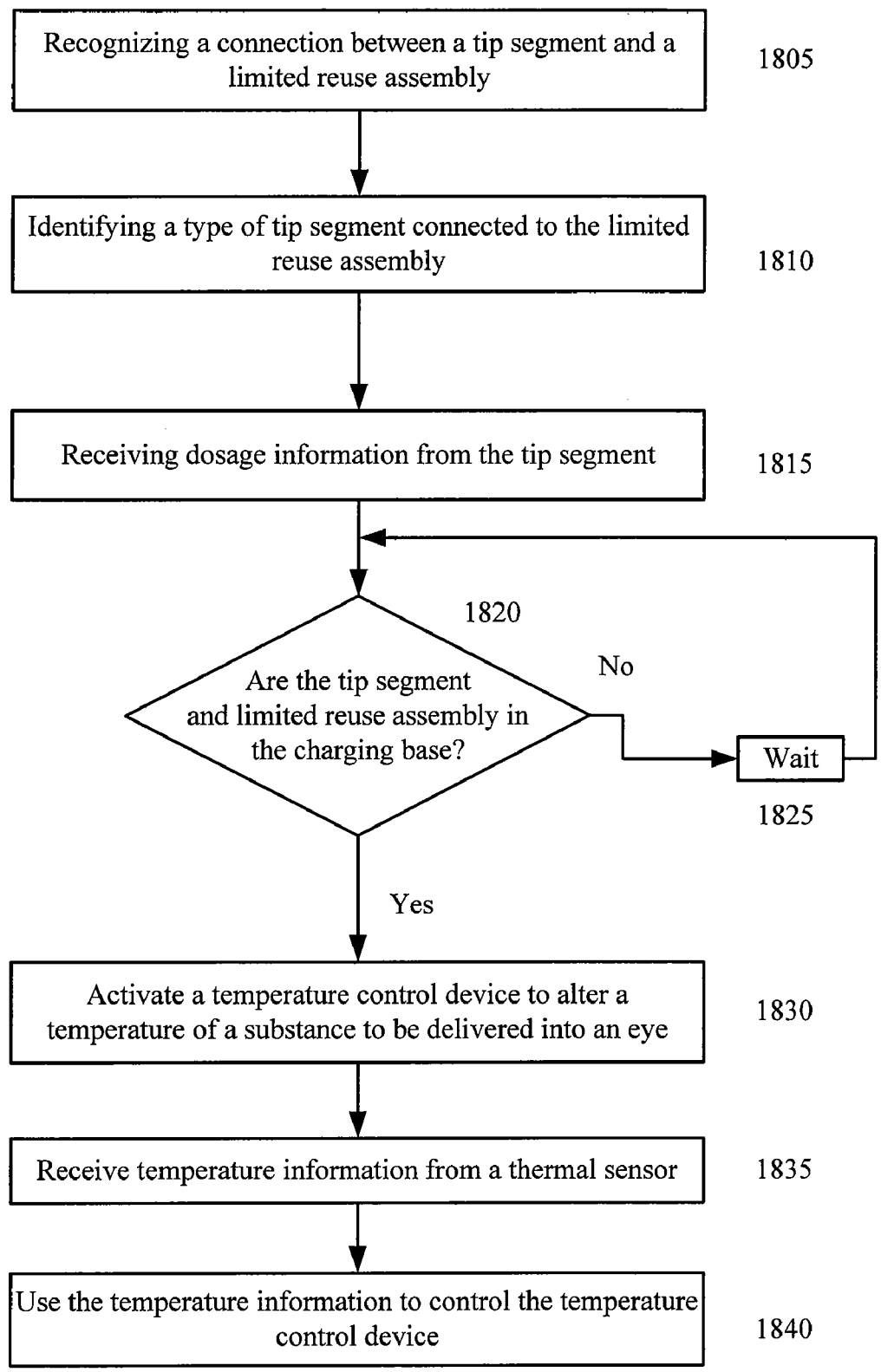
FIG. 18 is a flow chart of one method relating to injecting a substance into an eye according to the principles of the present invention.

FIG. 18 is a flow chart of one method relating to injecting a substance into an eye according to the principles of the present invention. FIG. 18 depicts a method of activating the temperature control device to heat or cool the substance located in the dispensing chamber while the tip segment and limited reuse assembly are located on a charging station. In 1805, a connection between a tip segment and a limited reuse assembly is recognized. In 1810, the type of tip segment is identified. In 1815, dosage information is received from the tip segment. In 1820, it is determined whether or not the tip segment and limited reuse assembly are located on the charging base. If they are not located on the charging base, then in 1825, the system waits and returns to 1820. If the tip segment and limited reuse assembly are located on the charging base, then in 1830, the temperature control device is activated to alter a temperature of the substance contained in the dispensing chamber. In 1835, temperature information is received from a thermal sensor. In 1840, this temperature information is used to control the temperature control device.

Figure 19:
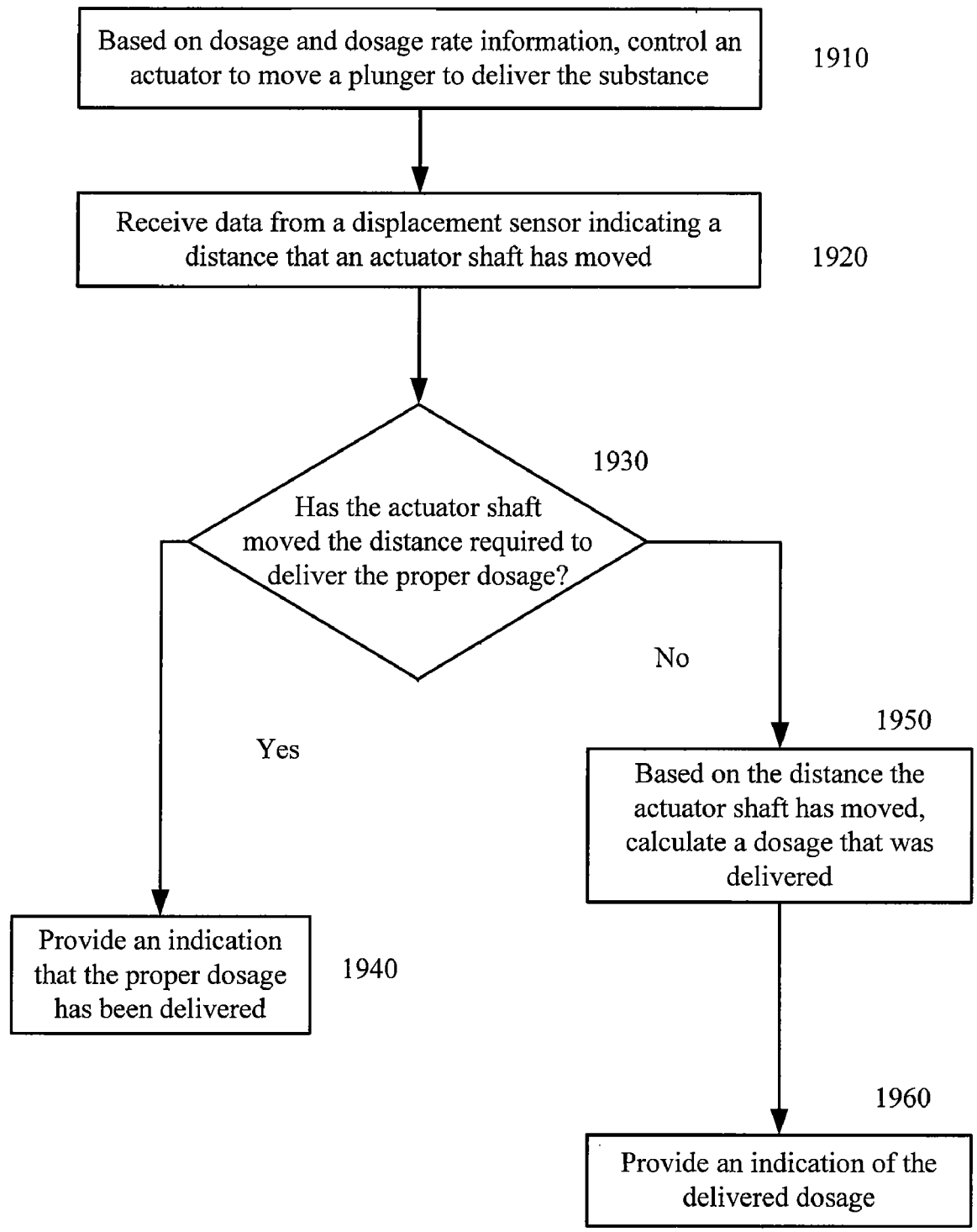
FIG. 19 is a flow chart of one method relating to injecting a substance into an eye according to the principles of the present invention.

FIG. 19 is a flow chart of one method relating to injecting a substance into an eye according to the principles of the present invention. FIG. 19 depicts a method relating to determining whether or not the proper dosage has been delivered. In 1910, the actuator is controlled based on a dosage and dosage rate information. The actuator moves the plunger to deliver the substance. In 1920, information is received from the displacement sensor indicating the distance that the actuator shaft has moved. In 1930, this distance information is used to determine if a proper dosage has been delivered. If the actuator shaft has moved the distance required to deliver the proper dosage, then in 1940, an indication that the proper dosage has been delivered is provided. If the actuator shaft has not moved the distance required to deliver the proper dosage, then in 1950, the dosage delivered is calculated based on the distance the actuator shaft has moved. In 1960, an indication of the delivered dosage is provided.

Figure 20:
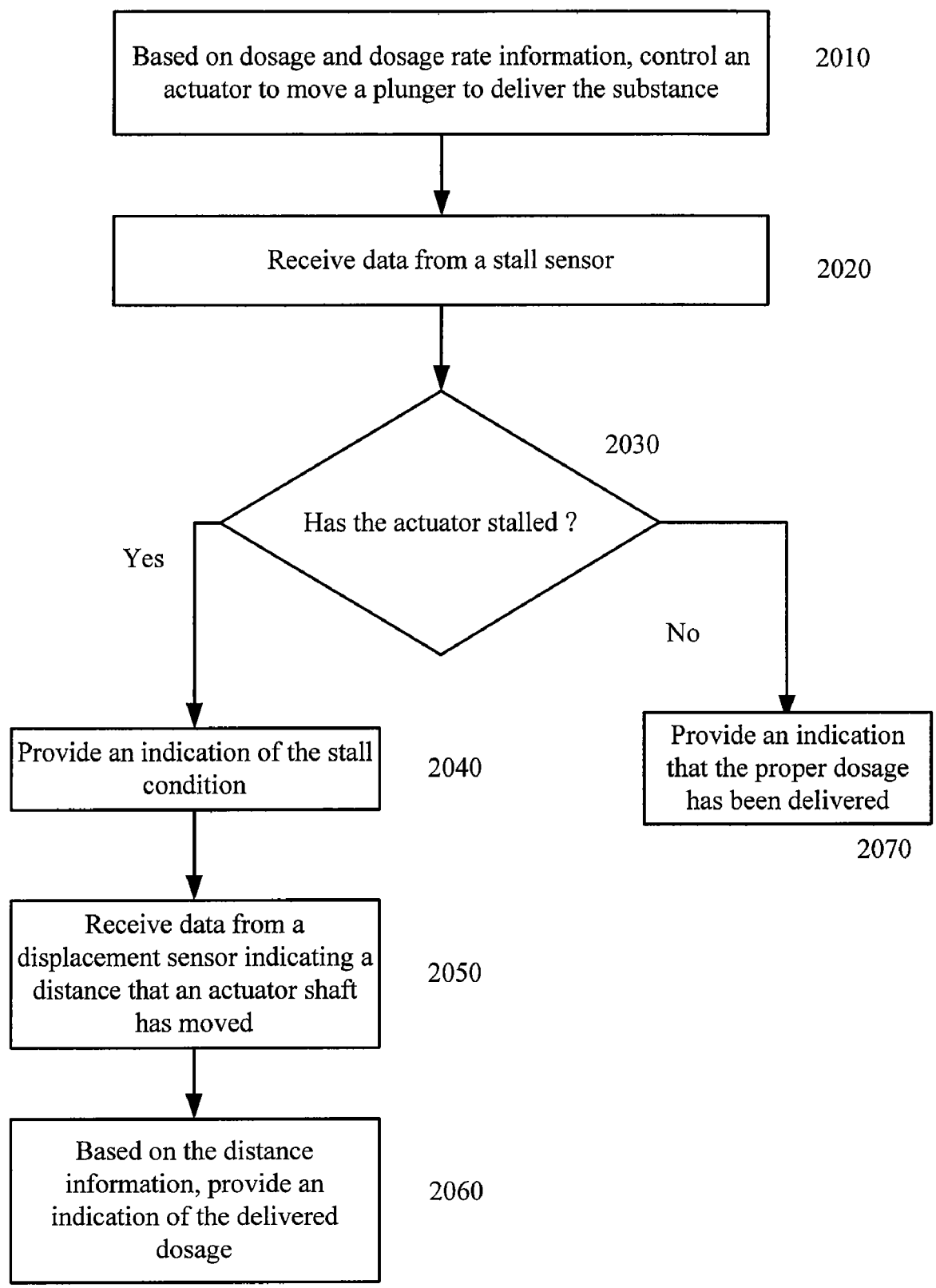
FIG. 20 is a flow chart of one method relating to injecting a substance into an eye according to the principles of the present invention.

FIG. 20 is a flow chart of one method relating to injecting a substance into an eye according to the principles of the present invention. FIG. 20 relates to the situation in which the actuator shaft has stalled. In 2010, the actuator is controlled based on a dosage and dosage rate information. The actuator moves the plunger to deliver the substance. In 2020, data is received from a stall sensor. In 2030, this data is used to determine if the actuator shaft has stalled. If the shaft has stalled, then in 2040, an indication of the stall condition is provided. In 2050, data is received from a displacement sensor indicating the distance that the actuator shaft moved. In 2060, an indication of the delivered dosage is provided based on the distance information. If the shaft has not stalled, then in 2070, an indication is provided that the proper dosage has been delivered.

From the above, it may be appreciated that the present invention provides an improved system and methods for delivering precise volumes of a substance into an eye. The present invention provides a single use, disposable delivery device tip segment that is capable of delivering a precise dosage. The tip segment interfaces with a limited reuse assembly. The present invention is illustrated herein by example, and various modifications may be made by a person of ordinary skill in the art.

While the present invention is described in the context of a single-use drug delivery device, the present invention encompasses any single-use medical device that interfaces with a source of electric power. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ophthalmic injection system comprising:
a tip segment attachable to and removable from a limited reuse assembly;
the tip segment comprising:
a dispensing chamber housing having an inner surface and an outer surface, the inner surface partially defining a dispensing chamber for holding a quantity of a substance;
a plunger engaged with the inner surface of the dispensing chamber housing, the plunger capable of sliding in the dispensing chamber housing, the plunger fluidly sealed to the inner surface of the dispensing chamber housing, the plunger having a plunger interface;
a needle fluidly coupled to the dispensing chamber;
a temperature control device at least partially surrounding the dispensing chamber housing, the temperature control device for altering a temperature of the substance in the dispensing chamber;
a thermal sensor located near the dispensing chamber housing, the thermal sensor for measuring a temperature near the dispensing chamber housing;
a memory device;
a first pair of tip interface connectors located on an interfacing surface of the tip segment, the first pair of tip interface connectors electrically coupled to the temperature control device;
a second pair of tip interface connectors located on the interfacing surface of the disposable injection device, the second pair of tip interface connectors electrically coupled to the thermal sensor;
a third pair of tip interface connectors located on the interfacing surface of the disposable injection device, the third pair of tip interface connectors electrically coupled to the memory device; and
a first housing at least partially enclosing the dispensing chamber housing, the temperature control device and the plunger
the limited reuse assembly comprising:
an actuator having a shaft;
a power source for providing power to the actuator;
a controller for controlling the actuator;
a mechanical linkage interface coupled to the shaft, the mechanical linkage interface having a mating surface on an end, the mating surface for interfacing with the plunger interface;
a pair of limited reuse assembly interface connectors located on an interfacing surface of the limited reuse assembly;
a displacement sensor for measuring a distance the actuator shaft travels;
an interface for connecting the displacement sensor to the controller; and
a second housing at least partially enclosing the power source, the controller, and the actuator;
wherein the substance is injected after the temperature of the substance is altered.

2. The system of claim 1 wherein:
the thermal sensor is connected to the controller via the second pair of tip interface connectors.

3. The system of claim 2 wherein the controller uses the temperature information to control the temperature control device.

4. The system of claim 2 wherein the controller uses the temperature information to control an injection of the substance.

5. The system of claim 1 wherein the thermal sensor is selected from the group consisting of a thermocouple and a thermistor.

6. The system of claim 1 wherein the temperature control device is a heater.

7. The system of claim 1 wherein the temperature control device is a cooling device.

8. The system of claim 1 wherein the temperature control device is a combination heating and cooling device.

9. The system of claim 1 wherein the limited reuse assembly further comprises:
   a stall sensor for detecting if the actuator is experiencing a stall condition; and
   an interface for connecting the stall sensor to the controller.

10. The system of claim 1 wherein the power source is a battery.

11. The system of claim 1 wherein the actuator is selected from the group consisting of: a stepper motor, a DC motor, a DC motor with a rotary sensor coupled to a linear drive, and a DC motor coupled to a linear drive with a linear sensor.

12. The system of claim 1 wherein the actuator is a spring driven mechanism.

13. The system of claim 1 wherein the actuator shaft is rigidly connected to the mechanical linkage interface.

14. The system of claim 1 wherein the actuator shaft is coupled to the mechanical linkage interface via a ball and socket joint.

15. The system of claim 1 wherein the tip segment further comprises:
   a fuse electrically connected to one of the first, second, or third pair of tip interface connectors.

16. The system of claim 15 wherein the fuse is blown thus preventing further use of the disposable injection device.

17. The system of claim 1 wherein the controller interfaces with the memory device.

18. The system of claim 1 wherein the memory device includes data about a condition of the tip segment.

19. The system of claim 17 wherein the controller uses the data about a condition of the tip segment to control an operation of the tip segment.

20. The system of claim 17 wherein the memory device includes dosage data.

21. The system of claim 20 wherein the controller uses the dosage data to control an operation of the tip segment.

22. The system of claim 20 wherein the controller uses the dosage data to control an operation of the actuator.

23. The system of claim 20 wherein the controller uses the dosage data to control an operation of the temperature control device.

24. The system of claim 1 wherein the controller determines a distance to move the plunger to deliver a dosage of a substance.

25. The system of claim 1 wherein the controller operates the actuator so that the actuator shaft moves at a fixed rate.

26. The system of claim 1 wherein the controller operates the actuator so that the actuator shaft moves at a variable rate.

27. The system of claim 1 wherein the memory device is embodied in an RFID tag located near an interfacing surface of the disposable injection device.

28. The system of claim 27 wherein the limited reuse assembly further comprises:
   an RFID reader located near an interfacing end of the limited reuse assembly, the RFID reader adapted to read information from the RFID tag.

29. The system of claim 1 wherein motion is transferred from the mechanical linkage interface to the plunger only in a single dispensing direction.

30. The system of claim 1 wherein the substance is a drug for treating a condition of the eye.

31. The system of claim 1 wherein an initial amount of the substance is preloaded in the dispensing chamber and a dosage of the substance comprising less than the initial amount is delivered by movement of the plunger in the dispensing chamber.

* * * * *